(12) United States Patent
Slates

(10) Patent No.: US 6,703,843 B2
(45) Date of Patent: Mar. 9, 2004

(54) DEVICE FOR DIGITALLY MEASURING ELECTRICAL IMPEDANCE

(75) Inventor: Richard D. Slates, Minden, NV (US)

(73) Assignee: Bently Nevada, LLC, Minden, NV (US)

( * ) Notice: Subject to any disclaimer, the term of this patent is extended or adjusted under 35 U.S.C. 154(b) by 0 days.

(21) Appl. No.: 10/445,520

(22) Filed: May 27, 2003

(65) Prior Publication Data

US 2003/0210036 A1 Nov. 13, 2003

Related U.S. Application Data

(62) Division of application No. 10/042,514, filed on Jan. 8, 2002, which is a division of application No. 09/425,830, filed on Oct. 22, 1999, now Pat. No. 6,346,807.

(51) Int. Cl.$^7$ .......................... G01R 25/06; G01R 27/02
(52) U.S. Cl. ...................................... 324/608; 324/607

(58) Field of Search .......................... 324/76.11, 76.12, 324/76.15, 76.21, 76.22, 207.11, 207.13, 207.15, 207.16, 207.17, 207.18, 207.19, 207.26, 644, 662, 603, 605, 607, 608; 702/64, 155, 158

(56) References Cited

U.S. PATENT DOCUMENTS 6,016,445 A * 1/2000 Baura .......................... 600/547

* cited by examiner

Primary Examiner—John B. Vigushin
Assistant Examiner—Russell M. Kobert
(74) Attorney, Agent, or Firm—Dennis A. DeBoo

(57) ABSTRACT

A digital eddy current proximity system including a digital impedance measuring device for digitally measuring the proximity probes impedance correlative to displacement motion and position of a metallic target object being monitored. The system further including a cable-length calibration method, an automatic material identification and calibration method, a material insensitive method, an inductive ratio method and advanced sensing characteristics.

11 Claims, 16 Drawing Sheets

DEVICE FOR DIGITALLY MEASURING ELECTRICAL IMPEDANCE

This application is a divisional application of U.S. Ser. No. 10/042,514, filed Jan. 8, 2002, pending, which is a divisional patent application of U.S. Ser. No. 09/425,830, filed Oct. 22, 1999, issued Feb. 12, 2002 as U.S. Pat. No. 6,346,807.

BACKGROUND OF THE INVENTION

Analog eddy current proximity systems which analyze and monitor rotating and reciprocating machinery are known in the art. These analog systems typically include a proximity probe located proximate a target object (e.g., a rotating shaft of a machine or an outer race of a rolling element bearing) being monitored, an extension cable and analog conditioning circuitry. The target, proximity probe (a non-contacting device which measures displacement motion and position of an observed conductive target material relative to the probe), extension cable and conditioning circuitry components are all designed to interact in such a way that a voltage output from the circuitry is directly proportional to a distance between the probe and the target. This distance is commonly referred to as "gap".

The interaction that takes place between these components is in accord with the following rules: First, the electrical impedance measured at the conditioning circuitry is the electrical combination of the target, the probe including an integral sensing coil and cable, the extension cable and the conditioning circuitry. This impedance is usually called the "Tank Impedance" or parallel impedance (Zp). Second, this tank impedance is linearized and converted into a voltage directly proportional to gap. Third, the conditioning circuitry measures impedance at a specific frequency that is a function of its own circuitry. Generally, the circuitry runs at the frequency where the reactive component of the tank impedance approaches zero. In other words, the circuitry is a resonant system, so the frequency of operation will be where the phase shift of the impedance is approximately zero degrees. In reality, the phase shift is not exactly zero due to, inter alia, manufacturing and component variations and tolerances of each analog system.

In order to compensate for these variations and tolerances, each analog system is required to be calibrated to have a parallel impedance which is as close as possible to a predefined ideal parallel impedance while remaining substantially unsusceptible to the multitude of variations and tolerances found in the target, probe, extension cable, and conditioning circuitry. Simultaneously, each analog system is calibrated to have a maximum sensitivity to changes in gap. Moreover, each system is generally required to be calibrated to monitor one specific target material.

These analog systems are also generally burdened by temperature variations in the target, the probe including the integral sensing coil and cable, the extension cable and the conditioning circuitry due to the severe temperature variations in rotating and reciprocating machinery environments. Thus, each system is required to be designed around a multitude of component tolerances to compensate for the severe temperature variations engendered in these environments. Furthermore, these analog systems must also be designed around the sensitivity to changes in the conductivity and permeability of the target, the sensing coil, and the cable, which can greatly effect the precision of these systems.

Moreover, interchangeability problems arise from variations in the target, probe, extension cable, and conditioning circuitry which cause the tank impedance (Zp) versus gap to vary slightly from nominal resulting in a proclivity towards, inter alia, variations in incremental scale factor (ISF), variations in average scale factor (ASF) and deviations from a straight line (DSL). The incremental scale factor (ISF), variations in average scale factor (ASF) and deviations from a straight line (DSL) are common ways to specify transducer performance as is well known in the art.

It is critical that the displacement motion or position between the target and the sensing coil of the proximity probe remains within the linear range of the proximity probe for providing accurate and reliable measurements over a wide range of circuit and environmental conditions in order to operate rotating and reciprocating machinery safely and efficiently. Heretofore, the ability to provide accurate and reliable measurements over a wide range of circuit and environmental conditions has been dependent on, inter alia, designing and manufacturing each production unit within close tolerances and going through laborious calibration methods to compensate for the circuit and environmental conditions.

For the foregoing reasons, there is a need for an eddy current transducer system that, inter alia, substantially eliminates the manufacturing and component variations and tolerances of the prior art analog systems, a system that provides correct gap reading for different target materials and a system which is easy to calibrate.

Additionally, there is a need to solve the general problem of compensating for temperature errors, temperature profiles of different target materials and changes in component conductivity and permeability in order to preclude anomalous behavior in eddy current transducer systems.

Furthermore, there is a need for an eddy current transducer system that has better linearity and interchangeability. Moreover, there is a need for an eddy current transducer system that does not require component changes when re-calibrated to a new or different target material.

SUMMARY OF THE INVENTION

The instant invention is distinguished over the known prior art in a multiplicity of ways. For one thing, the instant invention provides a unique digital system for digitally measuring an unknown electrical impedance. Additionally, the instant invention provides a digital proximity system that is a direct one for one replacement for existing analog eddy current proximity systems which is compatible with any existing (or future) eddy current proximity probe (a non-contacting device which measures displacement motion and position of an observed conductive or metallic target material relative to the probe) and extension cable assembly. Thus, the instant invention can directly replace the analog conditioning circuitry of prior art analog systems thereby eliminating the anomalies associated with manufacturing and component variations, and tolerances of these systems. Furthermore, the instant invention eliminates the laborious design and calibration methods required to calibrate prior art analog systems in order to compensate for manufacturing and component variations, tolerances and environmental conditions.

In one form, the instant invention provides a system which includes a unique voltage ratio apparatus and method for digitally measuring an unknown electrical component value. The system accomplishes this by digitizing a first voltage impressed across a serial coupling of a first electrical component and a second electrical component, and by digitizing a second voltage impressed across the second electrical component only. Each of the two digitized voltages is then convolved with digitized waveforms to obtain a first and a second complex voltage number. A ratio of the second complex number to a difference between the first and the second complex number is determined and multiplied by a known value of the first electrical component to determine the unknown value of the second electrical component. A resistance means having a known value can be employed as the first electrical component. The second electrical component can take the form of a proximity probe having an unknown impedance value which, when determined by the instant invention, can be correlated to a distance between the probe and a metallic target object being monitored by the probe. Iteratively repeating the voltage ratio method results in continuously digitally determining the unknown impedance values of the probe which can be directly correlated to the continuous displacement motion and position of the target being monitored relative to the probe. In one form, the digitally determined impedance values can be transformed into analog signals and used to trip alarms, circuit breakers, etc., when the signals are outside nominal operating ranges set by plant operators.

Additionally, the instant invention provides a system that can be used as a direct one for one replacement for existing (and future) analog eddy current proximity systems. The system includes a unique apparatus and method for digitally measuring the impedance of a proximity probe and an extension cable (if employed) which includes the unique voltage ratio apparatus and method delineated supra to obtain an unknown impedance of the proximity probe. Then, the system mirrors a circuit equivalent impedance of an existing (or future) analog proximity circuit and combines the measured impedance with the circuit equivalent impedance for defining a parallel or tank impedance. The defined tank impedance is then correlated to a distance between the probe and a metallic target object being monitored by the probe. Hence, the system can continuously digitally determine the unknown impedance value of the probe by iteratively repeating the aforementioned method and then correlate the digitally measured probe impedance values to the continuous displacement motion and position of the target for analyzing and monitoring rotating and reciprocating machinery.

More particularly, the instant invention provides a system which employs at least one eddy current proximity probe having a multi-axial probe cable coupled to a sensing coil located proximate a conductive target to be monitored. The sensing coil is coupled to ground and to a second terminal of a resistor via the probe cable and an extension cable (if employed). A first terminal of the resistor is coupled to a signal generator device that is digitally programmable to generate dynamic driving signals.

The signal generator device can be included in a digital feedback loop which includes means for monitoring the phase of the tank impedance and to provide corrective action (a frequency change) for adjusting that phase. Thus, the signal generator device can be digitally programmed to emulate the operating frequency of any previous (or future) analog proximity system and can also be digitally reprogrammed, in real time, for driving the sensing coil of the probe at one or more frequencies corrective of any anomalous phase shift calculated from the probe or tank impedance or due to any other anomalies within the system. For example, the instant invention can drive the sensing coil at a precise frequency corrective of temperature variations in the probe including the integral sensing coil and probe cable, and in the target.

A filter is interposed between the signal generator device and the first terminal of the resistor to purify the output dynamic signals of the signal generator device by eliminating, inter alia, harmonics that are created in the device. In addition, the filter helps reduce the noise bandwidth of the system which improves a signal to noise ratio. The filtered signal is driven through the resistor, extension cable (if employed), probe cable and coil for inducing eddy currents within the target. In turn, the eddy currents in the target induce a voltage in the sensing coil of the probe and hence, a change in an impedance of the probe and extension cable (if employed) which varies as a function of, inter alia, the displacement motion and position of the target relative to the probe.

The first and second terminals of the resistor are coupled to inputs of a first and a second analog to digital converter respectively. In turn, the outputs of the analog to digital converters are coupled to a digital signal processor including a convolution means. The first analog to digital converter receives and samples a first voltage between the serially coupled resistor, extension cable (if employed), probe cable and coil and outputs a first digital voltage signal to the digital signal processor. The second analog to digital converter receives and samples the voltage between ground and the combination of the extension cable (if employed), the probe cable and the coil and then, outputs a second digitized voltage signal to the digital signal processor. A timing control means is operatively coupled to the analog to digital converters and to the signal generator device such that the sampling is synchronously performed with the driving signal of the signal generator. This ensures, inter alia, that when the voltages are calculated there will be exactly one cycle worth of data stored in each data set.

The digital signal processor convolves the two digitized voltages by convolving each digitized voltage with a digital sine and cosine wave to obtain a first and a second complex voltage number. Once the convolution of the digitized voltages is performed the impedance value of the extension cable (if employed), probe cable and coil can be calculated directly from the measured voltages.

The system includes an open/short/load calibration method which can compensate for cable length included in the second electrical component. For example, the extension cable can be compensated for by using the open/short/load calibration method according to the instant invention. Thus, the system can apply the open/short/load calibration method to the measured impedance to obtain a compensated impedance. Furthermore, the open/short/load calibration method can be utilized to calibrate each printed wire assembly within the system.

The measured impedance or the compensated impedance is then correlated by the system to a gap value by using equations, numerical methods, algorithmic functions or lookup tables wherein gap values are correlated to measured or compensated impedance values defining the gap or spacing interposed between the probe and the target being monitored. This method of measuring gap can be continuously repeated for monitoring, for example the vibration of a rotating shaft of a machine or an outer race of a rolling element bearing.

Additionally, the system can combine the measured impedance or the compensated impedance value with a mathematical model value or an empirically predetermined value of an existing (or future) analog conditioning circuit that is compatible with the particular probe being employed. This value can be called up from a memory means associated with the digital signal processor. The digital signal processor combines this value with the measured impedance or the compensated impedance to obtain a resultant impedance defined as the tank impedance. This tank impedance can be employed to determine the gap between the probe and the target by using equations, numerical methods, algorithmic functions or lookup tables wherein gap values are correlated to tank impedance values. Thus, the existing proximity probe can be retained and this method of measuring gap can be continuously repeated for monitoring, for example the vibration of a rotating shaft of a machine or an outer race of a rolling element bearing that was heretofore monitored by an analog eddy current proximity system.

Gap values can be outputted to a digital to analog converter for providing analog outputs or downloaded to a processing stage for further processing and/or providing digital and/or analog outputs.

The impedance value of analog conditioning circuitry determined from the mathematical model or empirically is typically dependent on operating frequency. Thus, once the tank impedance is determined it can be used to determine if the system is running at the proper frequency. If the system is not running at the proper frequency the digital feedback loop can be used to feedback a signal from the digital signal processor to program the signal generator device for dynamically adjusting the driving signal.

Moreover, the instant invention includes a unique material identification method for automatically identifying a target material and automatically calibrating itself to monitor the identified material thereby eliminating the need for component changes and laborious re-calibration methods inherent with prior art systems. The instant invention also expands the unique material identification method to include a material insensitive method which is capable of outputting a gap value substantially correct for any target material being monitored thereby providing a material insensitive digital proximity system. Thus, the instant invention provides a digital proximity system that does not require component changes when being used to replace an existing system and/or does not require re-calibration when being used with a new or different target material. As a result, the instant invention provides a digital proximity system which can not be mis-calibrated when put into operation and which eliminates the interchangeability problem found in prior art systems.

Additionally, the instant invention includes a unique inductive ratio method which allows a gap versus inductive ratio curve to be determined for a specific target material without knowing the far gap impedance of the probe coil and thus, without removing the probe from a machine being monitored. The gap versus inductive ratio curve determined by this method can be used to determine the gap between the probe and the target being monitored. Furthermore, this method can be used to discern moisture ingress within a probe while it is still in the machine.

OBJECTS OF THE INVENTION

Accordingly, a primary object of the instant invention is to provide a new, novel and useful digital eddy current proximity system: apparatus and method.

Another further object of the instant invention is to provide is to provide a new, novel and useful digital system for measuring an unknown electrical value of an electrical component, for example, an unknown impedance value of an electrical component thereby providing a digital impedance measuring device.

Another further object of the instant invention is to provide a digital proximity system as characterized above which includes the digital impedance measuring device employed to measure impedance of an eddy current displacement probe and correlate the measured impedance to a gap between the probe and a target being monitored.

Another further object of the instant invention is to provide a digital proximity system as characterized above which includes means to dynamically measure the impedance of an eddy current probe at bandwidths high enough to support vibration information.

Another further object of the instant invention is to provide a digital proximity system as characterized above which provides a digital proximity system that is compatible with previous (or future) analog eddy current systems and existing signal conditioning sensors including proximity sensors using one or more frequencies.

Another further object of the instant invention is to provide a digital proximity system as characterized above which is capable of emulating the operation of analog conditioning circuitry of eddy current proximity systems for providing backwards (or future) compatibility with analog systems.

Another further object of the instant invention is to provide a digital proximity system as characterized above which includes an open/short/load calibration method which allow various cable length compatibility.

Another further object of the instant invention is to provide a digital proximity system as characterized above which includes a unique automatic material identification and calibration method.

Another further object of the instant invention is to provide a digital proximity system as characterized above which includes a unique material insensitive method.

Another further object of the instant invention is to provide a digital proximity system as characterized above which includes a unique inductive ratio method for measuring gap values.

Another further object of the instant invention is to provide a digital proximity system as characterized above which is self-contained, self-configuring and self-analyzing.

Another further object of the instant invention is to provide a digital proximity system as characterized above which is capable of identifying an eddy current displacement probe that is coupled thereto.

Viewed from a first vantage point, it is an object of the instant invention to provide a device for digitally measuring electrical impedance, comprising in combination: a network including a first electrical component and a second electrical component serially connected; a signal generating means operatively coupled to the network for driving a current through the serially connected components; means for sampling a first voltage impressed across the network and a second voltage impressed across the second component into digitized voltages; means for convolving each the digitized voltage with a digital waveform for forming a first complex number and a second complex number correlative to the first voltage impressed across the network and the second voltage impressed across the second component respectively; means for determining a ratio of the second complex number to a difference between the first and the second complex number, and means for calculating an electrical impedance of the second component by multiplying the ratio by a value of the first component wherein the electrical impedance of the second component is digitally measured.

Viewed from a second vantage point, it is an object of the instant invention to provide a method for digitally measuring electrical impedance, the steps including: forming a network including providing a first electrical component and a second electrical component serially connected; driving the network with a dynamic signal for impressing a voltage across the network and each component; digitizing the voltage across the network and the voltage across the second electrical component; convolving each of the digitized voltages with a digital waveform for forming a first complex number and a second complex number correlative to the voltages across the network and across the second electrical component respectively; determining a ratio of the second complex number to a difference between the first complex number and the second complex number; calculating an electrical impedance of the second electrical component by multiplying the ratio by a know digitized value of the first electrical component wherein the electrical impedance of the second component is digitally measured.

Viewed from a third vantage point, it is an object of the instant invention to provide an apparatus for determining a gap between a proximity probe and a conductive target material, the apparatus comprising in combination: a network including a first electrical component and a proximity probe serially connected; a signal generating means operatively coupled to the network for driving a current through the serial connection wherein a first analog voltage is impressed across the network and a second analog voltage is impressed across the proximity probe; means for sampling and digitizing the first analog voltage impressed across the network and the second analog voltage impressed across the proximity probe into digitized voltages; means for convolving each the digitized voltage with a digital waveform for forming a first complex number and a second complex number correlative to the first analog voltage impressed across the network and the second analog voltage impressed across the proximity probe respectively; means for determining a voltage ratio of the second complex number to a difference between the first complex number and the second complex number; means for processing the voltage ratio into a gap value correlative to a gap between the proximity probe and a conductive target material.

Viewed from a fourth vantage point, it is an object of the instant invention to provide an apparatus for determining a gap between a proximity probe and a conductive target material, the apparatus comprising in combination: a network including an extension cable interposed between and serially connected to a first electrical component and a proximity probe; a signal generating means operatively coupled to the network for driving a current through the serial connection wherein a first analog voltage is impressed across the network and a second analog voltage is impressed across the serial connection of the extension cable and the proximity probe; means for sampling and digitizing the first analog voltage impressed across the network and the second analog voltage impressed across the serial connection of the extension cable and the proximity probe into digitized voltages; means for convolving each the digitized voltage with a digital waveform for forming a first complex number and a second complex number correlative to the first analog voltage impressed across the network and the second analog voltage impressed across the serial connection of the extension cable and the proximity probe respectively; means for determining a voltage ratio of the second complex number to a difference between the first complex number and the second complex number; means for processing the voltage ratio into a gap value correlative to a gap between the proximity probe and a conductive target material.

Viewed from a fifth vantage point, it is an object of the instant invention to provide an apparatus for determining a dynamic gaps between a proximity probe and a conductive target material, the apparatus comprising in combination: means for establishing dynamic voltage signals correlative to dynamic gaps between a proximity probe and a conductive target material; sampling means for digitizing the established dynamic voltage signals into digital voltage signals; a digital multiplier for multiplying each the digital voltage signal by a digital sine signal and a digital cosine signal; means for accumulating values of each multiply in a memory, and means for processing each multiply for obtaining complex voltage representations correlative to dynamic gaps between the proximity probe and a conductive target material.

Viewed from a sixth vantage point, it is an object of the instant invention to provide a method for measuring a gap between a proximity probe and a conductive target material, the method including the steps of: providing a network of components including a first electrical component and a proximity probe component serially connected; driving a dynamic current through the serially connected electrical components for impressing a first analog voltage across the network and a second analog voltage cross the proximity probe component; sampling and digitizing the first analog voltage impressed across the serially connected resistance and probe components to obtain a first digitized voltage value; sampling and digitizing a second analog voltage impressed across the probe component to obtain a second digitized voltage value; digitally convolving the first digitized voltage and the second digitized voltage into a first complex number and a second complex number respectively; calculating a voltage ratio of the second complex number to a difference between the first complex number and the second complex number; processing the voltage ratio into a gap value correlative to a gap between the proximity probe and a conductive target material.

Viewed from a seventh vantage point, it is an object of the instant invention to provide a method for measuring a gap between a proximity probe and a conductive target material, the method including the steps of: providing a network of components including a first electrical component and a proximity probe component serially connected; driving a dynamic current through the serially connected electrical components including the resistance component and the proximity probe component for impressing a first analog voltage across the network and a second analog voltage cross the proximity probe component; sampling and digitizing the first analog voltage impressed across the serially connected resistance and probe components to obtain a first digitized voltage value; sampling and digitizing a second voltage impressed across the probe component to obtain a second digitized voltage value; digitally convolving the first digitized voltage and the second digitized voltage into a first complex number and a second complex number respectively; calculating a voltage ratio of the second complex number to a difference between the first complex number and the second complex number; multiplying the voltage ratio by a value of the first electrical component for determining an impedance of the proximity probe; correlating the determined impedance of the proximity probe to a gap between the proximity probe and a conductive target material.

Viewed from a eighth vantage point, it is an object of the instant invention to provide a method for measuring a gap between a proximity probe and a conductive target material, the method including the steps of: providing a network of components including a first electrical component, an extension cable component and a proximity probe component respectively serially connected, and locating the proximity probe adjacent a conductive target material; driving a dynamic current through the serially connected electrical components for impressing a first analog voltage across the network and a second analog voltage across the serial connection of the extension cable component and the proximity probe component; sampling and digitizing the first analog voltage impressed across the network to obtain a first digitized voltage value; sampling and digitizing a second analog voltage impressed across the serial connection of the extension cable component and the proximity probe component to obtain a second digitized voltage value; digitally convolving the first digitized voltage value and the second digitized voltage value into a first complex number and a second complex number respectively; calculating a voltage ratio of the second complex number to a difference between the first complex number and the second complex number; processing the voltage ratio into a gap value correlative to a gap between the proximity probe and the conductive target material.

Viewed from a ninth vantage point, it is an object of the instant invention to provide a method for measuring a position of a conductive target material, the steps including: sampling and digitizing a first voltage impressed across a serial connection of a resistance means and a proximity probe located adjacent a conductive target material to obtain a first digitized voltage; sampling and digitizing a second voltage impressed only across the probe to obtain a second digitized voltage, transforming the two digitized voltages into complex voltage numbers; calculating an electrical impedance of the proximity probe by using both complex voltage numbers; correlating the calculated electrical impedance to a gap between the proximity probe and the conductive target material.

Viewed from a tenth vantage point, it is an object of the instant invention to provide a method for measuring a gap between a proximity probe and a conductive target material, the steps including: sampling and digitizing a first voltage impressed across a serial connection of a first electrical component and a proximity probe located adjacent a conductive target material to obtain a first digitized voltage; sampling and digitizing a second voltage impressed across the probe to obtain a second digitized voltage, transforming the two digitized voltages into complex voltage numbers; determining an electrical impedance of the proximity probe by using both complex voltage numbers; normalizing the electrical impedance of the proximity probe; correlating the normalized electrical impedance of the proximity probe to a gap between the proximity probe and the conductive target material.

Viewed from a eleventh vantage point, it is an object of the instant invention to provide a method for measuring a gap between a proximity probe and a conductive target material, the steps including: sampling and digitizing a first voltage impressed across a serial connection of a first electrical component, an extension cable and a proximity probe located adjacent a conductive target material to obtain a first digitized voltage; sampling and digitizing a second voltage impressed across the probe to obtain a second digitized voltage, transforming the two digitized voltages into complex voltage numbers; determining an electrical impedance of the proximity probe by using both complex voltage numbers and compensating for the extension cable; normalizing the electrical impedance of the proximity probe; correlating the normalized electrical impedance of the proximity probe to a gap between the proximity probe and the conductive target material.

Viewed from a twelfth vantage point, it is an object of the instant invention to provide a method for measuring a gap between a proximity probe and a conductive target material, the method including the steps of: digitally measuring an electrical impedance of a proximity probe located adjacent a conductive target material; combining a predetermined digitized impedance with the digitally measured impedance of the proximity probe; correlating the combined impedance to a gap interposed between the proximity probe and the conductive target material being monitored.

Viewed from a thirteenth vantage point, it is an object of the instant invention to provide a method for measuring a gap between a proximity probe and a conductive target material, the method including the steps of: digitally measuring an electrical impedance of an a proximity probe and an extension cable connected thereto, the proximity probe is located adjacent a conductive target material; combining a predetermined digitized impedance with the digitally measured impedance; correlating the combined impedance to a gap interposed between the proximity probe and the conductive target material being monitored.

Viewed from a fourteenth vantage point, it is an object of the instant invention to provide a method for measuring a gap between a proximity probe and a conductive target material, the method including the steps of: measuring an impedance of a proximity probe located proximate a conductive target material and an extension cable operatively coupled to the proximity probe; compensating the measured impedance by using compensation coefficients stored in a memory means; combining a predetermined impedance with the compensated measured impedance for forming a combination impedance; determining a gap between the proximity probe and the conductive target material as a function of the combination impedance; iteratively repeating the measuring, compensating, combining and determining steps to substantially continuously monitor the gap between the probe and the target as a function of the combination impedance.

Viewed from a fifteenth vantage point, it is an object of the instant invention to provide a method for measuring a gap between a proximity probe and a conductive target material, the steps including: providing a database of normalized impedance curve representations for different conductive target materials; measuring an impedance of a proximity probe located proximate a conductive target material being identified; normalizing the measured probe impedance; utilizing the normalized probe impedance and the database of normalized impedance curve representations for identifying the conductive target material; determining a gap value between the proximity probe and the conductive target material from the normalized probe impedance and the identified target material.

Viewed from a sixteenth vantage point, it is an object of the instant invention to provide a method for measuring a gap between a proximity probe and a conductive target material, the steps including: providing a representation of a defined series of gap locus each representative of the same gap for different target materials; measuring an impedance of a proximity probe located proximate a conductive target material; normalizing the measured probe impedance; determining a gap value between the proximity probe and the conductive target material from the normalized probe impedance and the representation of the defined series of gap locus wherein the gap value is substantially correct for any conductive target material adjacent the proximity probe thereby providing a material insensitive method for measuring gap values between the proximity probe and different conductive target materials.

Viewed from a seventeenth vantage point, it is an object of the instant invention to provide a method for measuring a gap between a proximity probe and a conductive target material, the steps including: providing a representation of a defined series of gap locus each representative of the same gap for different target materials; measuring an impedance of a proximity probe located proximate a conductive target material, the proximity probe including a probe cable; compensating an impedance contribution of the probe cable from the measured probe impedance to define a measured coil impedance; normalizing the measured coil impedance; determining a gap value between the proximity probe and the conductive target material from the normalized coil impedance and the representation of the defined series of gap locus wherein the gap value is substantially correct for any conductive target material adjacent the proximity probe thereby providing a material insensitive method for measuring gap values between the proximity probe and different conductive target materials.

Viewed from a eighteenth vantage point, it is an object of the instant invention to provide a method for measuring a gap between a proximity probe and a conductive target material, the steps including: measuring a proximity probe impedance at a first frequency and a second different frequency, the proximity probe including an integral sensing coil; determining an impedance of the sensing coil from the measured proximity probe impedance at the first frequency and the second different frequency; dividing a reactance of the impedance of the sensing coil at the first frequency by the reactance of the impedance of the sensing coil at the second different frequency for defining an inductive ratio; correlating the inductive ratio to a value representative to a gap between the proximity probe and the conductive target material.

Viewed from a nineteenth vantage point, it is an object of the instant invention to provide a method for measuring a gap between a proximity probe and a conductive target material, the steps including: sampling and digitizing a first voltage impressed across a serial connection of a resistance means and a proximity probe located adjacent a conductive target material to obtain a first digital voltage correlative to the first voltage at a first frequency; sampling and digitizing a second voltage impressed only across the probe to obtain a second digital voltage correlative to the second voltage at the first frequency, digitally convolving the first digital voltage and the second digital voltage into a first complex voltage number and a second complex voltage number; calculating an electrical impedance of the proximity probe at the first frequency by using the first complex voltage number and the second complex voltage number; sampling and digitizing a third voltage impressed across the serial connection of the resistance means and the proximity probe located adjacent the conductive target material to obtain a third digital voltage correlative to the third voltage at a second frequency; sampling and digitizing a fourth voltage impressed only across the probe to obtain a fourth digital voltage correlative to the fourth voltage at the second frequency, digitally convolving the third digital voltage and the fourth digital voltage into a third complex voltage number and a fourth complex voltage number; calculating a complex electrical impedance of the proximity probe at the second frequency by using the third complex voltage number and the fourth complex voltage number; dividing a reactance of the calculated complex electrical impedance of the sensing coil at the first frequency by the reactance of the calculated complex electrical impedance of the sensing coil at the second different frequency for defining an inductive ratio; correlating the inductive ratio to a value representative to a gap between the proximity probe and the conductive target material.

Viewed from a twentieth vantage point, it is an object of the instant invention to provide a method for measuring a gap between a proximity probe and a conductive target material, the steps including: providing a proximity probe having a first end located adjacent a conductive target material and having a second end coupled to a first end of an extension cable; measuring an impedance at a second end of the extension cable; compensating the measured impedance by mathematically eliminating extension cable residuals from the measured impedance for defining a proximity probe impedance of the proximity probe; correlating the proximity probe impedance with a value representative of a gap between the proximity probe and the conductive target material.

Viewed from a twenty-first vantage point, it is an object of the instant invention to provide a method for measuring a gap between a proximity probe and a conductive target material, the steps including: providing an extension cable having two ends; determining a first impedance of the extension cable with one of the two ends opened for defining an open impedance; determining a second impedance of the extension cable with one of the two ends shorted for defining a short impedance; providing a proximity probe having an end located adjacent a conductive target material and having an opposite end coupled to one of the two ends of the extension cable; measuring an impedance at the other end of the extension cable; determining an impedance of the proximity probe as a function of the short impedance, the open impedance and the measured impedance for defining a proximity probe impedance; correlating the proximity probe impedance with a value representative of a gap between the proximity probe and the conductive target material.

Viewed from a twenty-second vantage point, it is an object of the instant invention to provide a method for measuring a gap between a proximity probe and a conductive target material, the steps including: providing an extension cable having two ends; determining a first impedance of the extension cable with one of the two ends opened for defining a open impedance; determining a second impedance of the extension cable with one of the two ends shorted for defining a short impedance; determining a third impedance of the extension cable with one of the two ends coupled to a load having a known value for defining a load impedance; providing a proximity probe having an end located adjacent a conductive target material and having an opposite end coupled to one of the two ends of the extension cable; measuring an impedance at the other end of the extension cable; determining an impedance of the proximity probe as a function of the short impedance, the open impedance, the load impedance and the measured impedance for defining the proximity probe impedance; correlating the proximity probe impedance with a value representative of a gap between the proximity probe and the conductive target material.

Viewed from a twenty-third vantage point, it is an object of the instant invention to provide a method for measuring a gap between a proximity probe and a conductive target material, the steps including: providing an extension cable having two ends; determining a first load impedance of the extension cable with one of the two ends coupled to a first load; determining a second load impedance of the extension cable with one of the two ends coupled to a second load; the second load having an impedance that is less than the impedance of the first load; providing a proximity probe having an end located adjacent a conductive target material and having an opposite end coupled to one of the two ends of the extension cable; measuring an impedance at the other end of the extension cable; calculating a proximity probe impedance of the proximity probe as a function of the measured impedance, the first load impedance and the second load impedance for compensating for extension cable residuals; correlating the proximity probe impedance with a value representative of a gap between the proximity probe and the conductive target material.

Viewed from a twenty-fourth vantage point, it is an object of the instant invention to provide a method for measuring a characteristic of a conductive target material disposed adjacent a proximity probe, the steps including: providing a length of cable having a first end and a second end; determining a first impedance of the cable with the first end opened for defining a open impedance; determining a second impedance of the cable with the first end shorted for defining a short impedance; coupling the first end of the cable to a proximity probe and having the second end of the cable coupled to a digital eddy current proximity system; measuring, at the second end of the cable, an impedance of the coupled cable and proximity probe; calculating the proximity probe impedance as a function of the measured impedance, the open impedance, and the short impedance for compensating for cable length residuals; correlating the proximity probe impedance with a characteristic of a conductive target material disposed adjacent the proximity probe.

These and other objects and advantages will be made manifest when considering the following detailed specification when taken in conjunction with the appended drawing figures.

DESCRIPTION OF PREFERRED EMBODIMENTS

Figure 1:
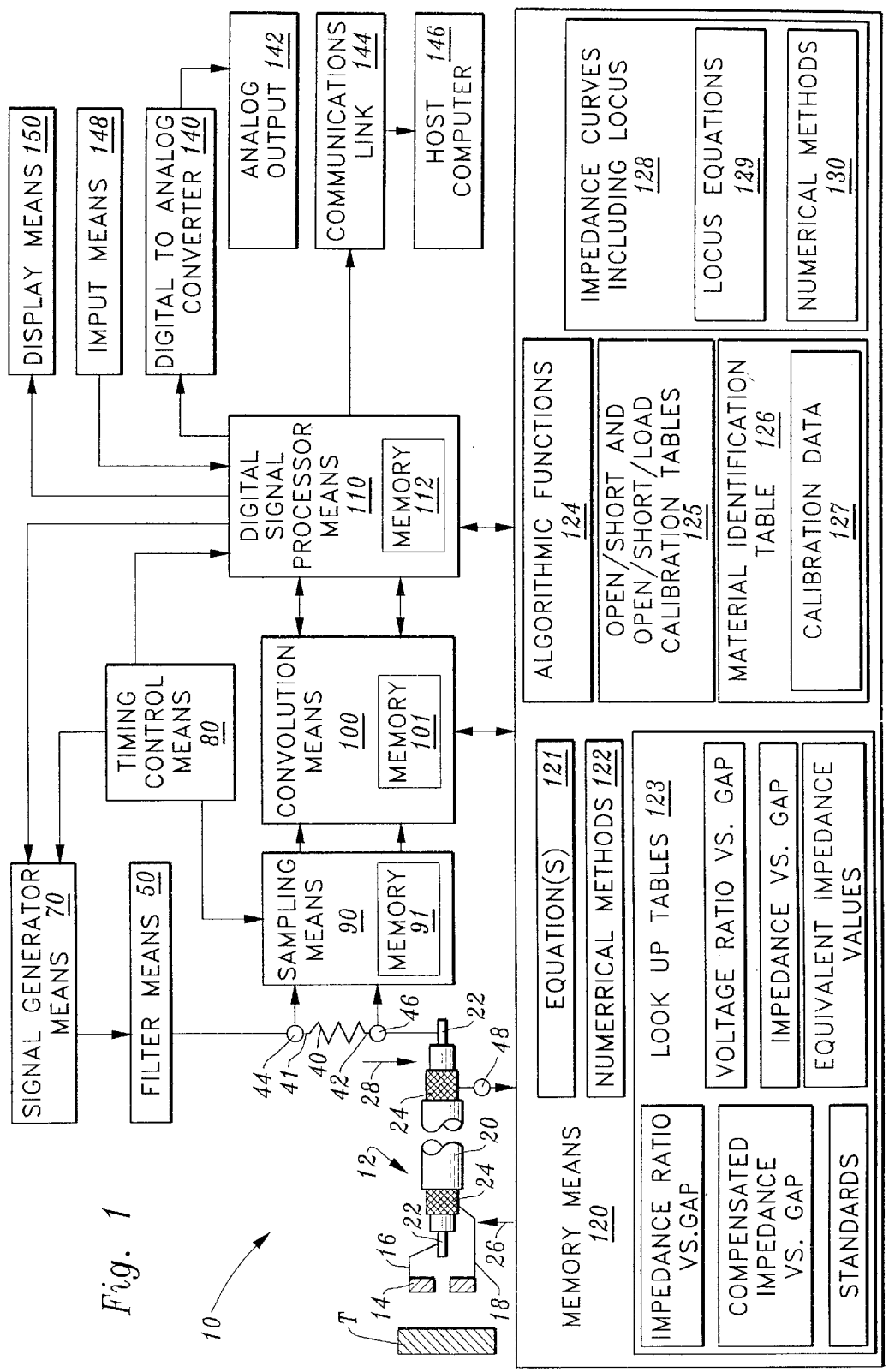
FIG. 1 is a block diagram of the digital proximity system according to the instant invention shown employing a proximity probe including a sensing coil located proximate a conductive target object to be monitored.
Figure 2:
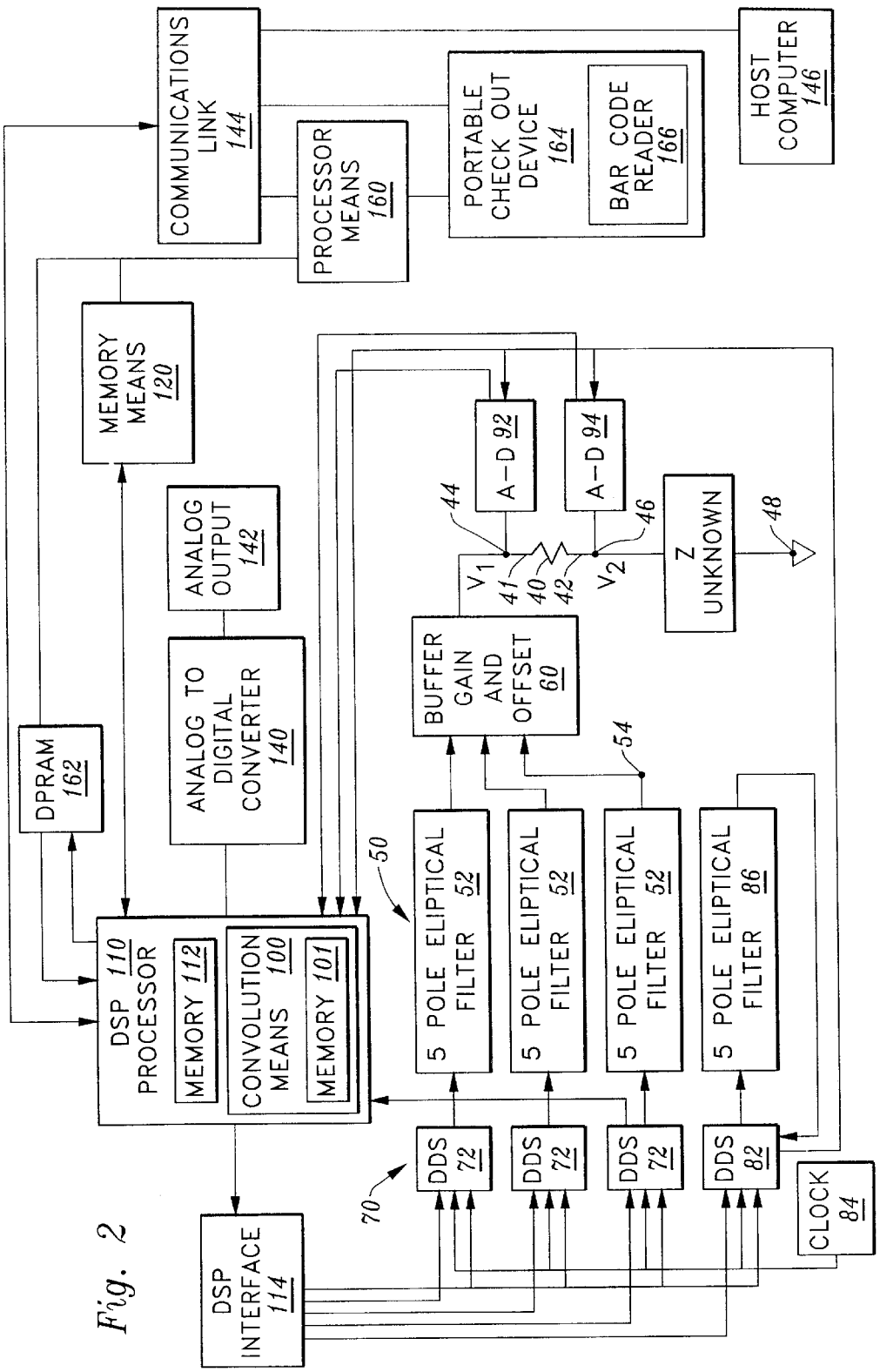
FIG. 2 is a block diagram of the digital proximity system according to the instant invention providing further detail.
Figure 3:
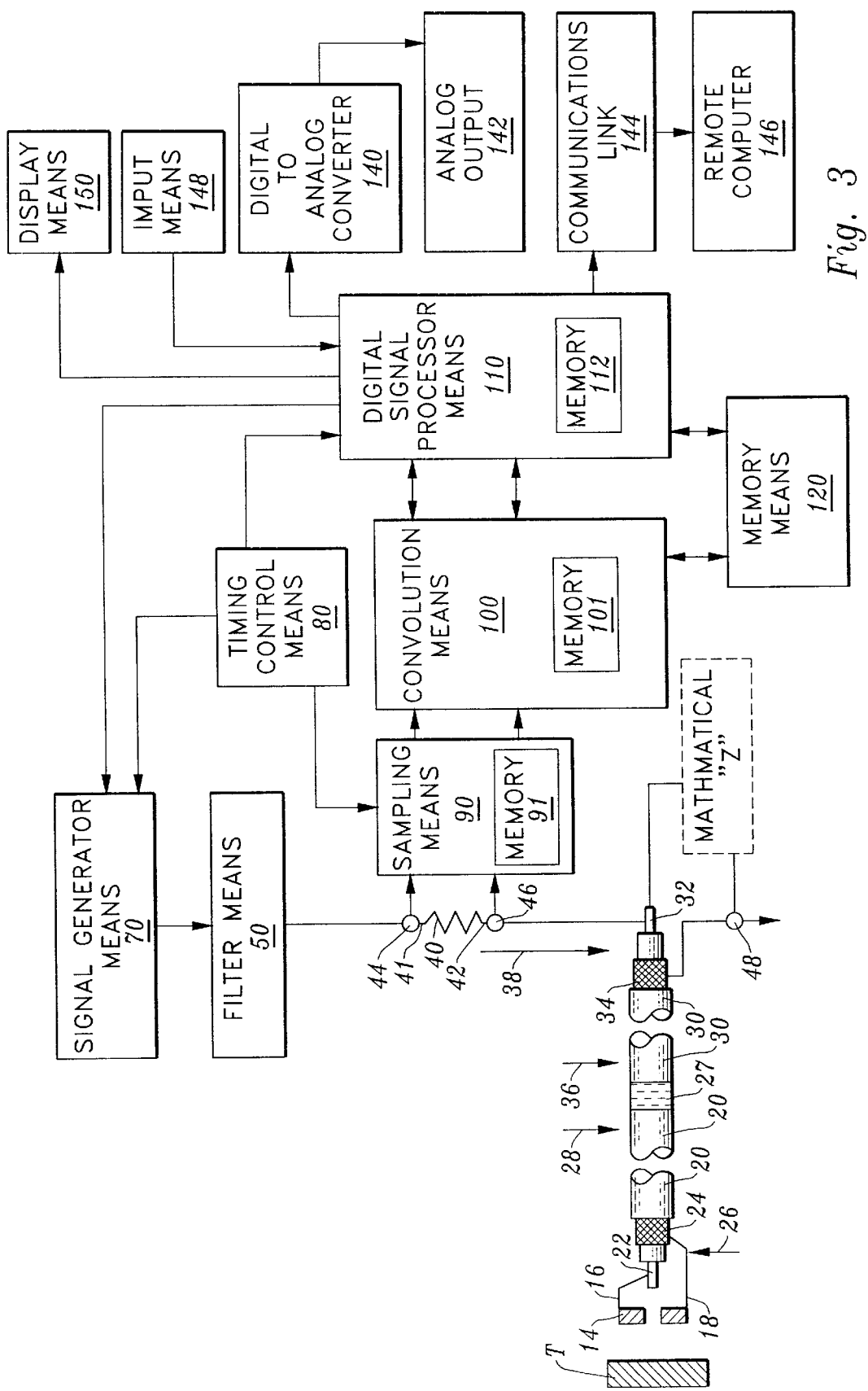
FIG. 3 is a block diagram of the digital proximity system according to the instant invention shown employing an extension cable.
Figure 4:
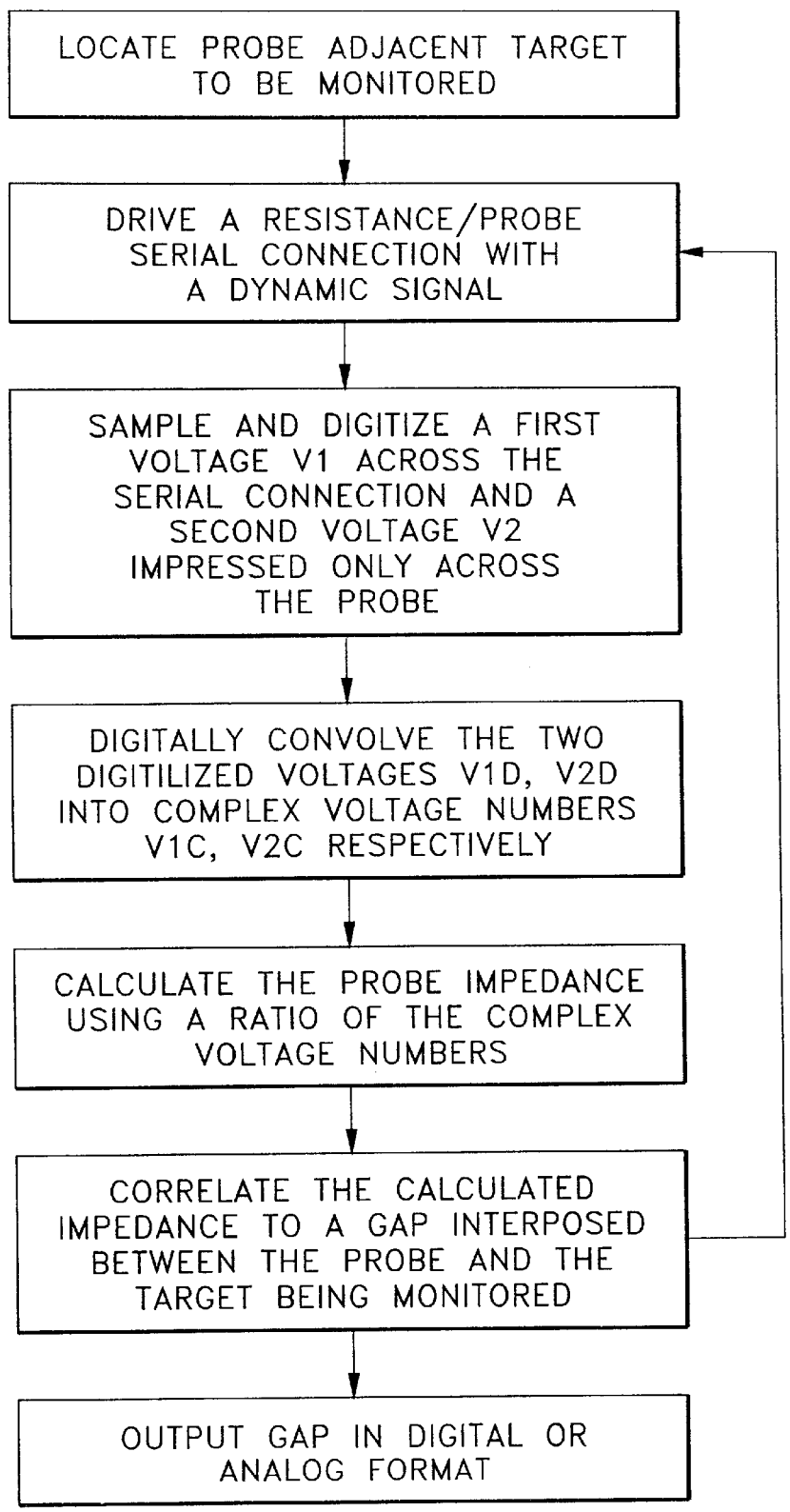
FIG. 4 is a flow chart of a voltage ratio method according to the instant invention.

Considering the drawings, wherein like reference numerals denote like parts throughout the various drawing figures, reference numeral 10 is directed to the digital proximity system according to the instant invention.

In its essence, and referring to FIGS. 1 through 4, the system 10 includes, inter alia, a unique voltage ratio apparatus and method (VR method) for digitally measuring an unknown electrical value of an electrical component. In one preferred form, the system 10 samples and digitizes a dynamic voltage $V_1$ impressed across a serial coupling of a first electrical component having a known electrical value and a second electrical component having an unknown electrical value. Additionally, the system 10 samples and digitizes a dynamic voltage $V_2$ impressed only across the second electrical component. These two digital voltages are then digitally convolved by the system 10 into complex voltage numbers $V_{1C}$ and $V_{2C}$ respectively. A ratio of the second complex number to a difference between the first and the second complex number is then determined by the system 10. The system 10 can use this voltage ratio to determine the unknown electrical value of the second electrical component. For example, and according to the instant invention, the system 10 can employ a proximity probe as the second electrical component and continuously digitally measure an impedance value of the probe monitoring, for example, a rotating shaft of a machine or an outer race of a rolling element bearing. The digitally measured impedance values can then be correlated by the system 10 to displacement motion and position of the rotating shaft or the outer race of the rolling element bearing relative to the probe for monitoring machinery status.

Specifically, and referring to FIGS. 1 through 4 the system 10 employs a proximity probe 12 which is disposed proximate a conductive or metallic target object T (e.g., a rotating shaft of a machine or an outer race of a rolling element bearing) to be monitored. The system 10 samples and digitizes a voltage $V_1$ impressed across a serial coupling of a resistance means 40 having a known electrical resistance value R and the proximity probe 12 (and, when employed, an extension cable 30 coupled to the probe 12) having an unknown electrical value $Z_{unknown}$ into a digital voltage $V_{1D}$. Additionally, the system 10 samples and digitizes a voltage $V_2$ impressed only across the proximity probe 12 (and coupled extension cable when employed) into a digital voltage $V_{2D}$. The system 10 then digitally convolves the two digital voltages $V_{1D}$, $V_{2D}$ into first and second complex voltage numbers $V_{1C}$ and $V_{2C}$ respectively. Then, the system 10 determines a ratio of the first complex number to a difference between the first and the second complex number and multiplies this voltage ratio by the known electrical resistance value R to determine the unknown impedance value $Z_{unknown}$ of the probe 12. This process follows the equation $Z_{unknown}=[V_{2C}/(V_{1C}-V_{2C})]*R$. The determined impedance $Z_{unknown}$ can then be compensated by using an open/short or open/short/load calibration or compensation method according to the instant invention which will be described in detail infra. The system 10 then correlates the determined impedance or the compensated determined impedance to a gap interposed between the probe disposed proximate the metallic target object T being monitored. Iteratively repeating the voltage ratio method results in continuously determining the unknown impedance values of the probe which can be correlated into values representative of the displacement motion and position of the metallic target object T relative to the probe. Thus, the system 10 according to the instant invention can be employed as, inter alia, a digital proximity system for continuously monitoring rotating and reciprocating machinery.

More particularly, and referring to FIGS. 1 through 4, the digital proximity system 10 includes the unique voltage ratio method (VR method) for digitally measuring the unknown electrical impedance of the probe 12 operatively coupled to the system 10 and strategically coupled to a machine for sensing raw dynamic data that is correlative to the spacing between the probe and the conductive or metallic target object T (e.g., a rotating shaft of a machine or an outer race of a rolling element bearing) being monitored. The digital proximity system 10 includes the resistance means 40 having a value R, a filter means 50, a buffer, gain and offset means 60 and a signal generator means 70. The digital proximity system 10 further includes a timing control means 80, a sampling means 90, a convolution means 100 and a digital signal processor (DSP) means 110.

The resistance means 40 includes a first terminal 41 and a second terminal 42 respectively coupled between a first node 44 and a second node 46. The proximity probe 12 includes an unknown dynamic probe impedance having a value $Z_{unknown}$ and is coupled between the second terminal 42 of the resistance means 40 at node 46 and a ground node 48. Thus, the resistance means 40 and the probe 12 form a serial connection.

The probe 12 includes an integral sensing element or coil 14 and a multi-conductor probe cable 20. The sensing element 14 includes a first electrical lead 16 and a second electrical lead 18. The probe cable 20 includes a first conductor 22 and a second conductor 24 extending from a first end 26 to a second end 28 of the probe cable 20. The first conductor 22 and the second conductor 24 at the first end 26 of the cable 20 are operatively coupled to the first electrical lead 16 and the second electrical lead 18 of the sensing element 14 respectively. The first conductor 22 at the second end 28 of the cable 20 is coupled to the second terminal 42 of the resistance means 40 at node 46 and the second conductor 24 is coupled to the ground node 48 thereby grounding one lead of the unknown dynamic probe impedance $Z_{unknown}$. It is important to note that the configuration of the resistance means and the unknown probe impedance $Z_{unknown}$ is neither arbitrary nor inconsequential. The configuration of the instant invention grounds a conductor of the probe so as to not have both conductors varying thereby eliminating, inter alia, signal changes within the probe due to, for example, external influences such as one moving or grabbing the cable. Furthermore, the unknown probe impedance $Z_{unknown}$ is digitally measured by direct read circuitry which takes direct voltage readings rather then inferring the voltage across or the current through the probe.

Additionally, the instant invention can employ a multi-conductor extension cable 30 (please see FIG. 3) for extending the distance between the proximity probe 12 and the system 10. The extension cable 30 includes a first conductor 32 and a second conductor 34 extending between a first end 36 and a second end 38 of the extension cable 30. The extension cable 30 is coupled between the probe cable 20 and the system 10. Particularly, the first end 36 of the extension cable 30 is coupled to the second end 28 of the probe cable 20 via a cable coupling 27 such that the conductor 22 is connected to conductor 32 and conductor 24 is connected to conductor 34. The first conductor 32 at the second end 38 of the cable 30 is coupled to the second terminal 42 of the resistance means 40 at node 46 and the second conductor 34 is coupled to the ground node 48. Thus, the extension cable 30 is coupled in series with the probe cable 20.

The signal generator means 70 is, operatively coupled to the first terminal 41 of the resistance means 40 at node 44 for driving a signal through the resistance means 40, and the probe 12 thereby impressing the first voltage $V_1$ across the serially connected resistance means 40 and probe 12, and impressing the second voltage $V_2$ only across the probe 12 (and extension cable if employed). Preferably, the signal generator means 70 is operatively coupled to the resistance means 40 at node 44 via the filter means 50 and to the digital signal processor for driving a programmable dynamic signal of one or more frequencies through the filter means 50 and the serial connection of the resistance means/probe combination.

In particular, the signal generator means 70 preferable includes a direct digital synthesis (DDS) device 72 operatively coupled to the first terminal 41 of the resistance means 40 via the filter means 50 and the buffer, gain and offset means 60 for driving the dynamic signal or waveform through the resistance means 40 and the probe 12 (and extension cable if employed). This dynamic signal causes the first voltage $V_1$ to be impressed across the serial connection of the resistance means 40 and probe 12 and causes the second voltage $V_2$ to be impressed only across the probe 12 (and extension cable if employed). Typically, the sensing element 14 of the probe 12 is strategically coupled proximate the target to be monitored such that this dynamic signal causes the sensing element 14 of the probe 12 to generate an alternating magnetic field that induces eddy currents in the metallic target object T. In turn, the eddy currents in the target induce a voltage in the sensing element 14 of the probe 12 and hence, a change in an impedance of the probe which varies as a function of, inter alia, variations of spacing or gap between the probe and the target being monitored.

The signal generator means 70 can include a plurality of DDS devices 72 coupled to the first terminal 41 of the resistance means 40 via the filter means 50 and the buffer, gain and offset means 60 for driving a plurality of dynamic signals at different frequencies through the resistance means 40, the probe 12 and extension cable (if employed) and subsequently performing processing including convolution as delineated in detail infra for obtaining simultaneous impedance measurements of the probe 12 at different frequencies which are correlative to the gap interposed between the probe 12 and the target being monitored.

Each direct digital synthesis device 72 is preferably coupled to the DSP means 110 via interface 114 and generates a pure frequency/phase-programmable dynamic signal such as a sinusoidal wave. The DSP means 110 preferably includes an algorithm to program both the frequency and the phase of the output signals which in turn can be used to drive the probe with a frequency/phase-programmable dynamic analog signal having an output frequency/phase which can be precisely manipulated under full digital control. Thus, each DDS device can be digitally programmed to output sine waves at any frequency/phase with precision for use as driving signals or reference signals. One example of the DDS devices 72 is that which is manufactured by Analog Devices and sold under part number AD9850.

The filter means 50 is interposed between the DDS devices 72 and the resistance means 40 for filtering the analog dynamic signals output from DDS devices 72. The filter means 50 preferably includes at least one low pass filter 52 interposed between each direct digital synthesis device 72 and the first terminal 41 of the resistance means 40 to purify the output dynamic signals or waveforms of each synthesis device 72 for eliminating, inter alia, the harmonics that are created in the synthesis devices 72. For example, as a result of the outputs of the direct digital synthesis devices 72 being ten plus bit digital to analog converters, the quantitization noise needs to be filtered out using a low pass filter. Thus, the filters 52 remove the steps and smoothes out the analog dynamic signal outputs from the DDS devices 72. Additionally, the filters 52 helps reduce the noise bandwidth of the system 10 which improves a signal to noise ratio. Furthermore, a half bit of noise can be summed in at node 54 to change the quantitization noise using a dithering process. Preferably the low pass filters 52 are in the form of five pole elliptical filter devices.

Buffer, gain and offset means 60 can be interposed between filter means 50 and the resistance means 40 for buffering and amplifying the analog dynamic signals and providing any desired offset of same.

The sampling means 90 is coupled to the first node 44 for sampling and digitizing the first voltage $V_1$ impressed across the serially connected resistor/probe combination. Additionally, the sampling means 90 is coupled to the second node 46 for sampling and digitizing the second voltage $V_2$ impressed only across the probe 12 (and extension cable if employed). Preferably, the sampling means 90 includes a pair of analog to digital converters 92, 94 coupled to the first node 44 and the second node 46 respectively for sampling and digitizing the first dynamic voltage $V_1$ and the second dynamic voltage $V_2$. The analog to digital (A-D) converters 92, 94 are preferably 14 bit, wide bandwidth converters manufactured by, for example, Analog Devices under part number AD9240.

The timing control means 80 provides the synchronization between the output signal of the signal generator means 70 and the sampling rate of the sampling means 90 so that the phase relationship between the output signal and samples is maintained. The timing control means 80 is operatively coupled to each DDS device 72, the pair of analog to digital converters 92, 94, and to the DSP means 110. Thus, the DDS devices 72 are clocked by the timing control means 80 so that the frequency of the output of these devices is very accurately set. Additionally, the timing control means 80 provides the synchronization between the output of the DDS devices 72 and the sampling rate of the analog to digital converters 92, 94 so that the phase relationship between the dynamic driving signal(s) and the sampled signals is maintained. Thus, the sampling is performed in synchrony with the dynamic driving signals. Note that the quartz clock oscillator 84 is operatively coupled to each DDS device 72 for providing a clock signal thereto.

Specifically, the timing control means 80 is an agile-clock generator which preferably includes a DDS device 82 operatively coupled to and clocked by a quartz clock oscillator 84. An output of the DDS device 82 is preferable filtered by a five pole elliptical filter 86 and feedback to the DDS device 82 which then outputs a triggering signal to the analog to digital converters 92, 94 and a timing signal to the DSP means 110. The DSP means 110 is operatively coupled to the DDS devices 72, 82 and may employ the timing signal sent to the DSP means 110 when digitally programming the DDS devices 72, 82 to orchestrate the synchronicity between the sampling rate and the dynamic signals output by the DDS devices 72 to the probe 12. This assures that when the voltages $V_{1D}$ and $V_{2D}$ are calculated there will be exactly one cycle worth of data stored per data set. Thus, the DDS devices can be used for generating the dynamic signals which excite the sensing element 14 and for generating timing signals for triggering the sampling by the pair of analog to digital converters 92, 94.

The convolution means 100 can be a stand-alone device in the form of, for example, a digital down counter (DDC), that just does convolution. In this embodiment, the convolution means 100 is interposed between and coupled to the sampling means 90 and the DSP means 110 to do the convolution operation. The analog to digital converted values (the digitized voltage signals $V_{1D}$, $V_{2D}$ which represent the dynamic voltages $V_1$ and $V_2$ at respective nodes 44 and 46) are received and convolved by the convolution means 100 and then supplied to the DSP means 110 as complex voltage numbers $V_{1C}$, $V_{2C}$. The advantage of this embodiment is that it is no longer necessary to vary the sample rate to remain synchronized to the signal generator. The DDC has the capability of being programmed for what frequency to process. One example of a commercially available digital down counter (DDC) is manufactured by Harris Semiconductor under part number HSP 50016.

Alternatively, the digital convolution means 100 can be integrally formed with the digital signal processor means 110 wherein the DSP means 110 is operatively coupled to the pair of analog to digital converters 92, 94 for receiving the first and second digitized voltage signals $V_{1D}$, $V_{2D}$ from the converters and convolving the digitized voltages into respective complex voltage numbers $V_{1C}$, $V_{2C}$ via the integral convolution means 100. Examples of DSP means 110 having integral convolution means 100 can be found in the 210XX series of devices manufactured by Analog Devices. Preferably, the DSP means 110 is a 40megahertz floating point device or faster.

The process of convolving the digitized voltages into respective complex voltage numbers $V_{1C}$, $V_{2C}$ via the convolution means 100 is defined as inphase and quadrature detection or quadrature synthesis.

Figure 5:
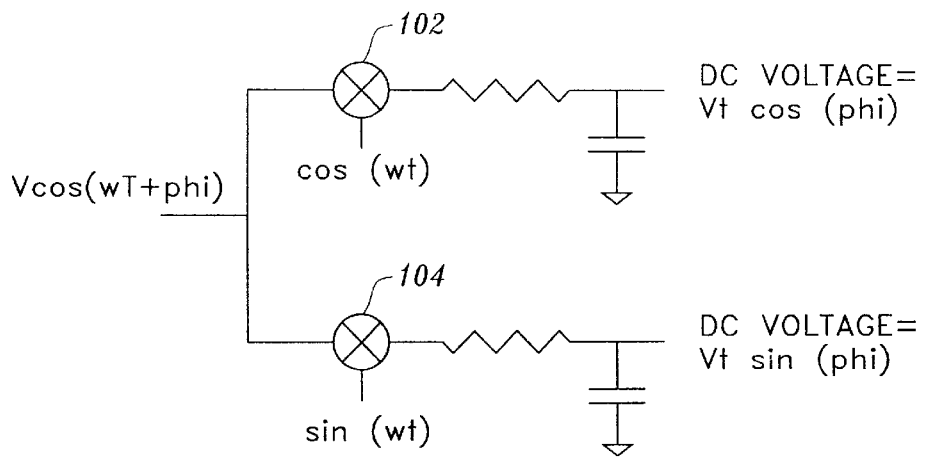
FIG. 5 is a diagrammatical view of a convolution block of the digital proximity system according to the instant invention.

More specifically, and referring to FIG. 5, the digitized voltage signals $V_{1D}$, $V_{2D}$ can be represented by the function Vcos(wT+phi) and the circles with the "X" in the middle represent digital multipliers 102,104 integrally formed in the convolution means 100. The digitized voltage signals $V_{1D}$, $V_{2D}$ are each multiplied by a digital cosine and sine waveform (cos(wT) and sin(wT)) which can be pulled from a table in memory 101, memory 112 or from memory means 120. The results of those multiples are accumulated and averaged or filtered by, for example, the convolution means 100 or the digital processor means 110 to get DC components. These filtered (averaged) values or transformed values represent the magnitude of real and imaginary components of the complex voltages $V_{1C}$, $V_{2C}$ of the convolved digitized voltage signals $V_{1D}$, $V_{2D}$. In other words, these DC components are the inphase and quadrature components of the digitized voltage signals $V_{1D}$ and $V_{2D}$ and represent magnitudes of real and imaginary components thereby forming complex voltage numbers $V_{1C}$ and $V_{2C}$ from the dynamic voltage signals $V_1$ and $V_2$.

An alternative way of looking at this is that when you multiply a signal (e.g. either of the data strings coming out of the analog to digital converters tied to node 44 ($V_1$) or node 46 ($V_2$) by a sine or a cosine wave of the same frequency, you get a DC term and a 2× AC term. Averaging the output of the multiplication then filters out the AC term. When this multiplication is performed using both a cosine and a sine function, you get two DC terms that represent the inphase and quadrature components of the signal. These are the real and the imaginary values for voltage. Note, a scaling term is usually needed after the averaging to get back to other proper engineering units. However, the term cancels out since voltage appears in both the numerator and denominator as a result of the instant invention using the voltage ratio method defined hereinabove.

Another possible way to implement the convolution method as contemplated by the instant invention is to interpose a Field Programmable Gate Array (FPGA) between the analog to digital converters and the DSP means 110. The difference between this configuration and that described hereinabove for the convolution device is that the structure of the hardware necessary to perform convolution method is built and programmed into the Field Programmable Gate Array (FPGA).

At this point it is important to note that the idea of using digital convolution means 100 is paramount because if the multipliers where to be of an analog design, the accuracy of the multipliers becomes a critical error source. For example, if one needs to distinguish a value of 0.005 in something of magnitude 300+j100 then a required stability at 1 MHz would be on the order of 1 part in 63,000. This is one to two orders of magnitude better than you can get out of an analog multiplier. Thus, the instant invention solves this problem by using analog to digital converters for sampling the voltage signals $V_1$ and $V_2$ and then performing multiplication in digital format to handle the stability problem. Additionally, the instant invention employs high speed analog to digital converters to avoid the additional error source (multiplier gain drift).

Once the complex voltage numbers $V_{1C}$ and $V_{2C}$ are determined, the digital signal processor means 110 processes the complex voltage numbers into the unknown impedance of the probe by preferably using the voltage ratio equation: $Z_{unknown}=[V_{2C}/(V_{1C}-V_{2C})]*R$. The DSP means 100 can continuously accumulate, process and store data from the convolution means 100 and output signals as a function of the calculated impedance which are correlative to the gap between the probe and the target (e.g., a rotating shaft of a machine or an outer race of a rolling element bearing) being monitored. Particularly, the calculated impedance can be converted by the processor 110 into a voltage or gap value correlative to the spacing or gap between the probe and target being monitored by using equation(s), algorithms, numerical methods or lookup tables stored in, for example, the memory means 120. It is important to note that the voltage ratio alone can be used to determine values representative of gap by accounting for the known resistance value within the equation(s), algorithms, numerical methods or look up tables.

Moreover, the digital signal processor can apply digital signals to the signal generator means 70 for digitally reprogramming, in real time, the generator means 70 for driving the probe 12 at one or more frequencies corrective of anomalies due to, for example: temperature variations; changes in the conductivity and permeability in the target, proximity probe (including the integral sensing coil and probe cable) and extension cable, and anomalies due to phase shift ascertained from the measured impedance values.

In addition to the unique voltage ratio method, the digital proximity system 10 includes a unique resonant method which emulates the operation of analog eddy current proximity systems thereby providing both backwards and forwards compatibility with existing and future analog systems. Thus, the digital proximity system 10 provides a direct one for one replacement of existing and future analog eddy current proximity systems.

For background, and as delineated in the background of the invention, a typical analog eddy current proximity system includes a proximity probe located proximate a metallic target object (e.g., a rotating shaft of a machine or an outer race of a rolling element bearing) being monitored, an extension cable (if employed) and analog conditioning circuitry which includes a resonate circuit. The target, probe, extension cable and conditioning circuitry are all designed to interact in such a way that a voltage output from the circuitry is directly proportional to a distance from the probe to the target and this distance is commonly referred to as "gap".

Figure 9:
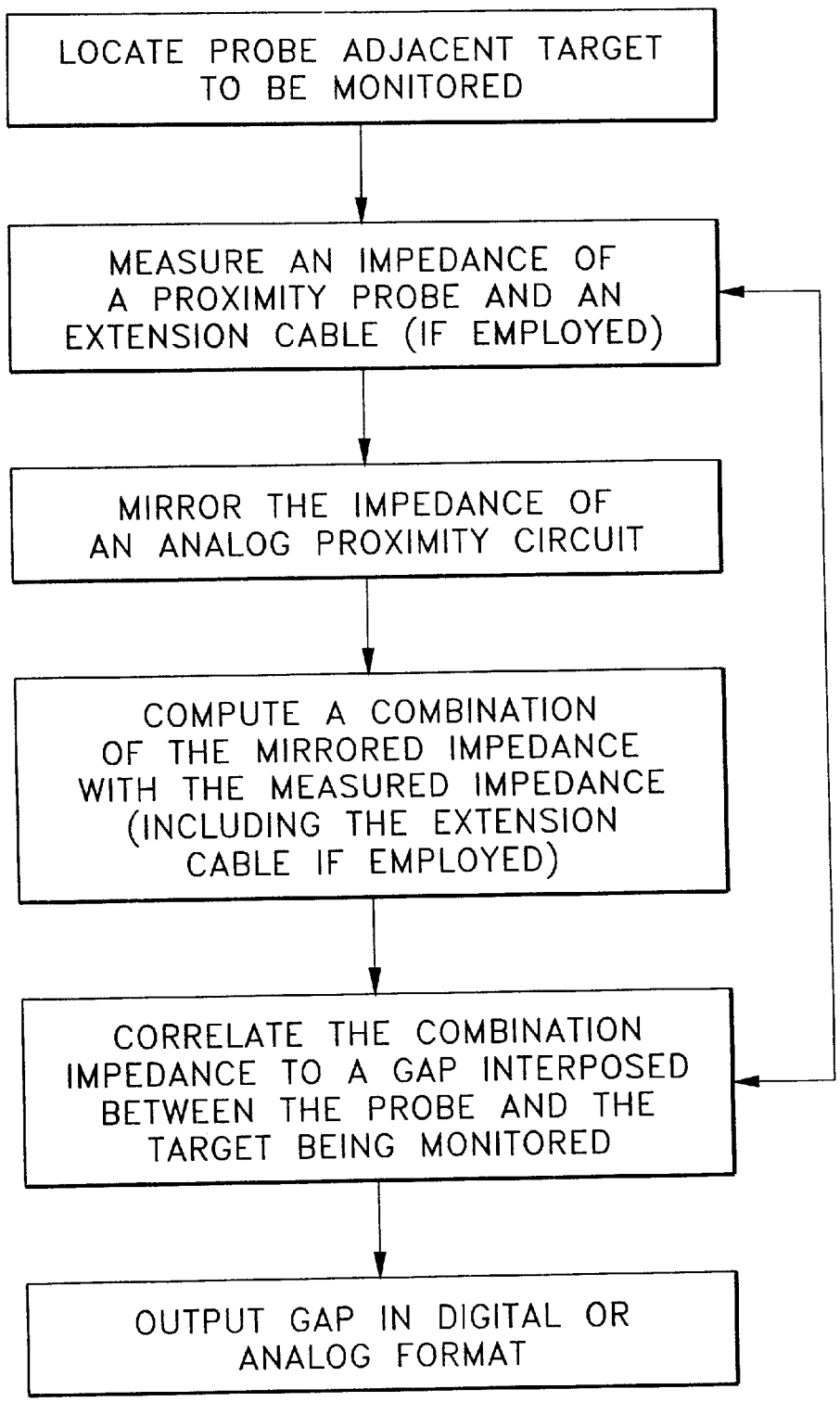
FIG. 9 is a general flow chart of a resonant method according to the instant invention.

In general, and referring to FIG. 9, the resonant method includes the steps of measuring the impedance of the probe and the extension cable (if employed), mirroring the impedance of analog proximity circuitry, computing a combination of the mirrored impedance with the measured probe and extension cable impedance (if employed), and determining a gap value as a function of the computed impedance which is correlative to the spacing or gap interposed between the probe and a metallic target being monitored. It should be understood that if the extension cable is not employed the system 10 would then only measure the impedance of the probe and compute the combination of the mirrored impedance with that of the measured probe impedance.

In particular, and referring to FIGS. 1 through 4, the digital Proximity system 10 uses the unique voltage ratio apparatus and method as delineated in detail hereinabove to first determine a complex number that represents the complex impedance of any probe and extension cable (if employed) that is new or that was previously coupled to an analog conditioning circuitry input. The complex number that represents the complex impedance of the probe and extension cable can be held in a memory such as the memory of the DSP means 110 and/or the memory means 120 which may or may not be integral with the DSP means 110.

Next, the system 10 mimics the loading that an analog conditioning circuit puts on a tank impedance of an included resonate circuit. The system 10 does this by putting a mathematical inductor and/or capacitor (mathematical Z) in parallel with the probe and extension cable impedance (please see FIG. 3). Therefore, the system 10 accurately mimics what happens in an actual analog conditioning circuitry for accomplishing the important task of providing backwards compatibility with the existing, field installed, transducers.

Figure 6:
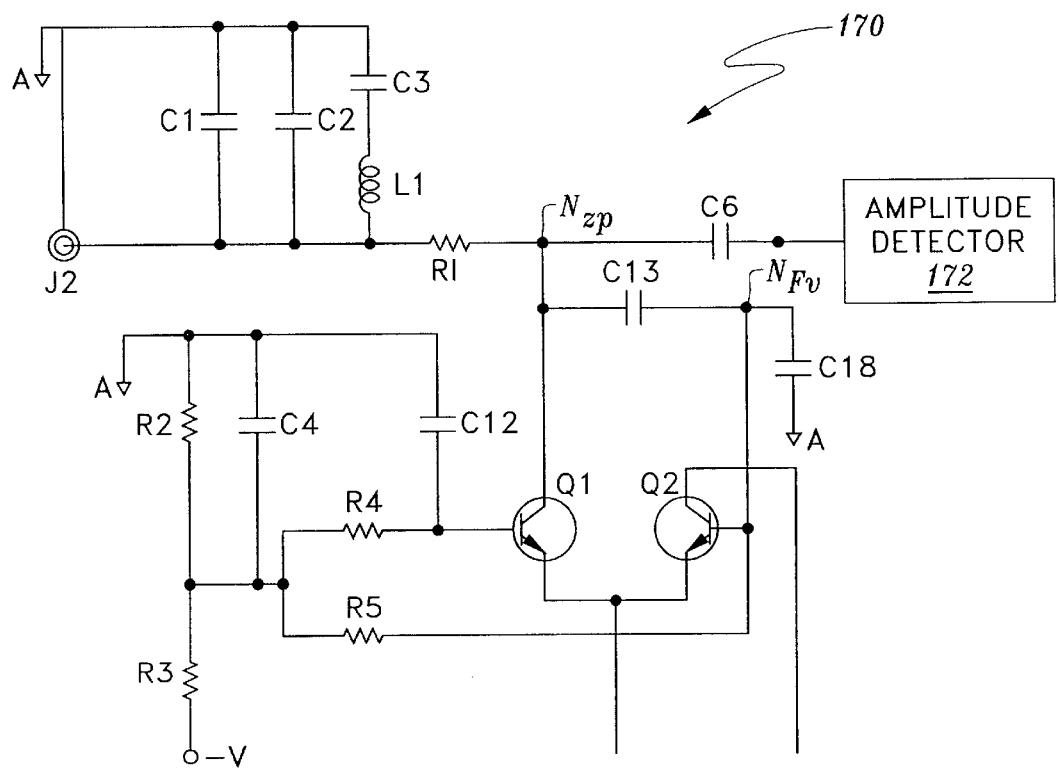
FIG. 6 is a schematic of an example of analog conditioning circuitry of an analog eddy current proximity system.

One way of explaining how the system 10 mirrors or mimics the analog conditioning circuitry is by example. The schematic shown in FIG. 6 shows one example of an analog conditioning circuit 170 having a resonate circuit and those having ordinary skill in the art and informed by the present disclosure should recognize the following:

First, that there is considerable circuitry in the analog conditioning circuitry that is in parallel with the impedance of the probe and/or extension cable at connector J2 which affects the magnitude of the impedance and the frequency of operation.

Second, that the current driven into the tank impedance at node $N_{Zp}$ is supplied from a collector of Q1.

Third, that the voltage at the collector of Q1 will be the tank impedance times the current supplied or in other words, the voltage at the collector of Q1 is directly proportional to the magnitude of the tank impedance that is to be measured. Thus, the actual value for the tank impedance (Zp) will be determined at the collector of Q1.

Fourth, that there is a transfer function from the collector of Q1 to a typical amplitude detector 172 in analog eddy current proximity systems.

Fifth, that there is a transfer function from the collector of Q1 to the feedback of the oscillator and that this feedback affects the frequency of operation.

Therefore, according to the instant invention, one method for mirroring or accurately mimicking analog circuitry in the digital proximity system 10 includes determining an equivalent impedance of the analog conditioning circuitry, for example the equivalent impedance of the analog conditioning circuitry 170.

The equivalent impedance may be determined by, for example, determining the equivalent circuit of the analog conditioning circuitry, pre-computing the impedance at different frequencies and using a look up table (stored in memory 112 or memory means 120) to grab the appropriate impedance value or any other method of determining circuit impedance which is known in the art. The first method provides the convenience of allowing one to verify a mathematical model versus what the system really does while the second method is more computationally efficient. Note that empirical testing may be required to match the actual system response to the mathematical model.

Figure 7:
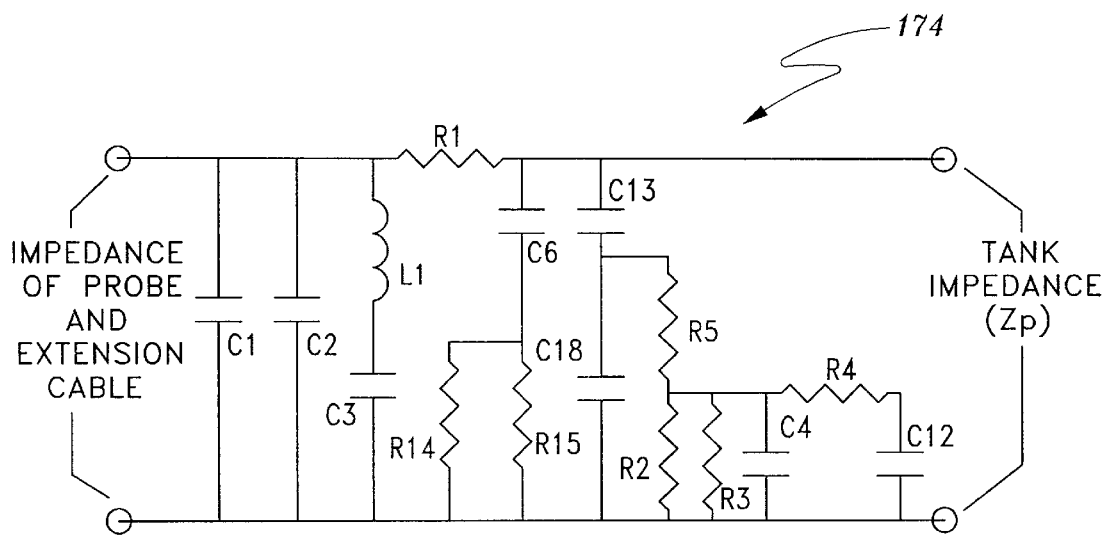
FIG. 7 is a schematic showing an equivalent circuit of the analog conditioning circuitry shown in FIG. 6.

For example, FIG. 7 shows a thevenin equivalent circuit 174 of that which is shown in FIG. 6. Some of the components therein have negligible contribution to the overall impedance, but it is preferred to add them for completeness. Some other impedances that may have a minor impact on computing Zp are, for example, the base impedance of the transistors.

Therefore, according to the instant invention, the combination of the impedance of the probe and extension cable (if employed) and the equivalent impedance of the analog conditioning circuitry 170 is then computed. This computed value is the tank impedance (Zp) and is correlated by the system 10 to a gap value by using equation(s), numerical methods, algorithmic functions or lookup tables wherein impedance values are correlated to gap values defining the gap or spacing interposed between the probe and the target being monitored. This method of measuring gap can be continuously repeated for monitoring, for example the vibration of a rotating shaft of a machine or an outer race of a rolling element bearing.

Figure 8:
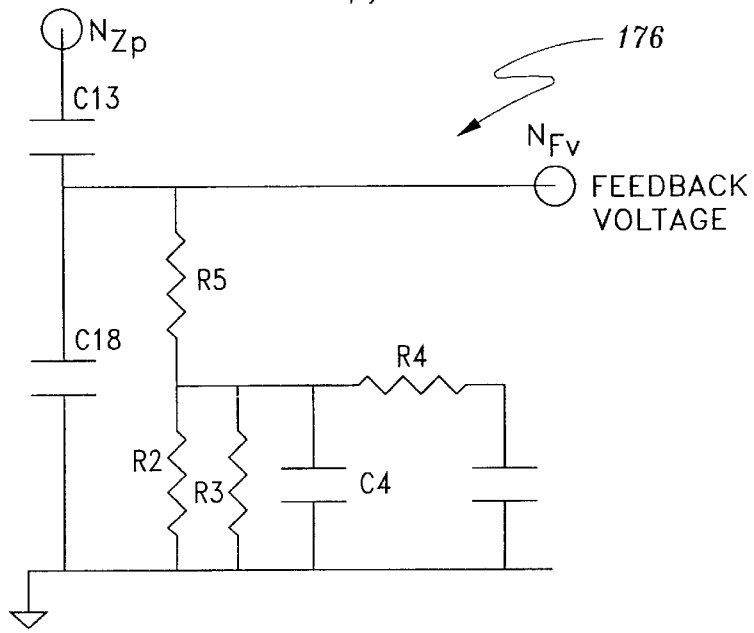
FIG. 8 is a partial schematic of that which is shown in FIG. 7 for showing where a feedback voltage is applied within the analog conditioning circuitry.

Notwithstanding, one design question that should be answered is whether the analog system is at the right frequency. The voltage developed at the collector of Q1 is assumed to be directly proportional to the tank impedance so it is exactly in phase with the voltage developed. This voltage is feedback to the base of Q2 to make the analog system oscillate, so it goes through the feedback network 176 shown in FIG. 8.

The phase shift from the node marked $N_{Zp}$ to the feedback voltage node $N_{Fv}$ is the phase delay of the oscillator. This phase shift is added to the phase of the tank impedance and should equal the phase of the oscillator under steady-state operation. If there is an inequality, the oscillator is not at steady state and will slew towards the frequency that satisfies that relationship. To account for this the digital proximity system 10 computes a phase error which is defined by the following equation: Phase error=phase the oscillator runs at (usually 0 to 6 degrees)−Phase of the tank impedance+the phase delay in the feedback network. Preferably, the digital proximity system 10 multiplies this calculated phase error by a pre-computed gain term to compute how far to adjust the frequency to mimic steady state operation of the analog circuitry. This calculation can be computed in the DSP means 110. Thus, a digital feedback loop including the signal generator means 70 can receive digital feedback signals from the digital signal processor means 110 which are correlative to any anomalous phase error ascertained from the measured impedance for digitally reprogramming, in real time, the generator means 70 for driving the sensing coil 14 of the probe 12 which adjusts the frequency to mimic steady state operation of the analog circuitry.

Thus, the digital proximity system 10 may have to account for the frequency shift before it can compute the gap of the system.

Typically, the components used in the analog conditioning circuitry are called out on bill of materials (BOMs) and installed into the printed wiring assemblies (PWAs). The Zp versus gap is set when the resistors are tweaked during calibration of the analog conditioning circuitry. In the digital Proximity system 10, these values are mathematical constructs stored in a file in the memory means 120 and pulled out as needed to work with whatever device the system 10 happens to be plugged into at the time.

Figure 10:
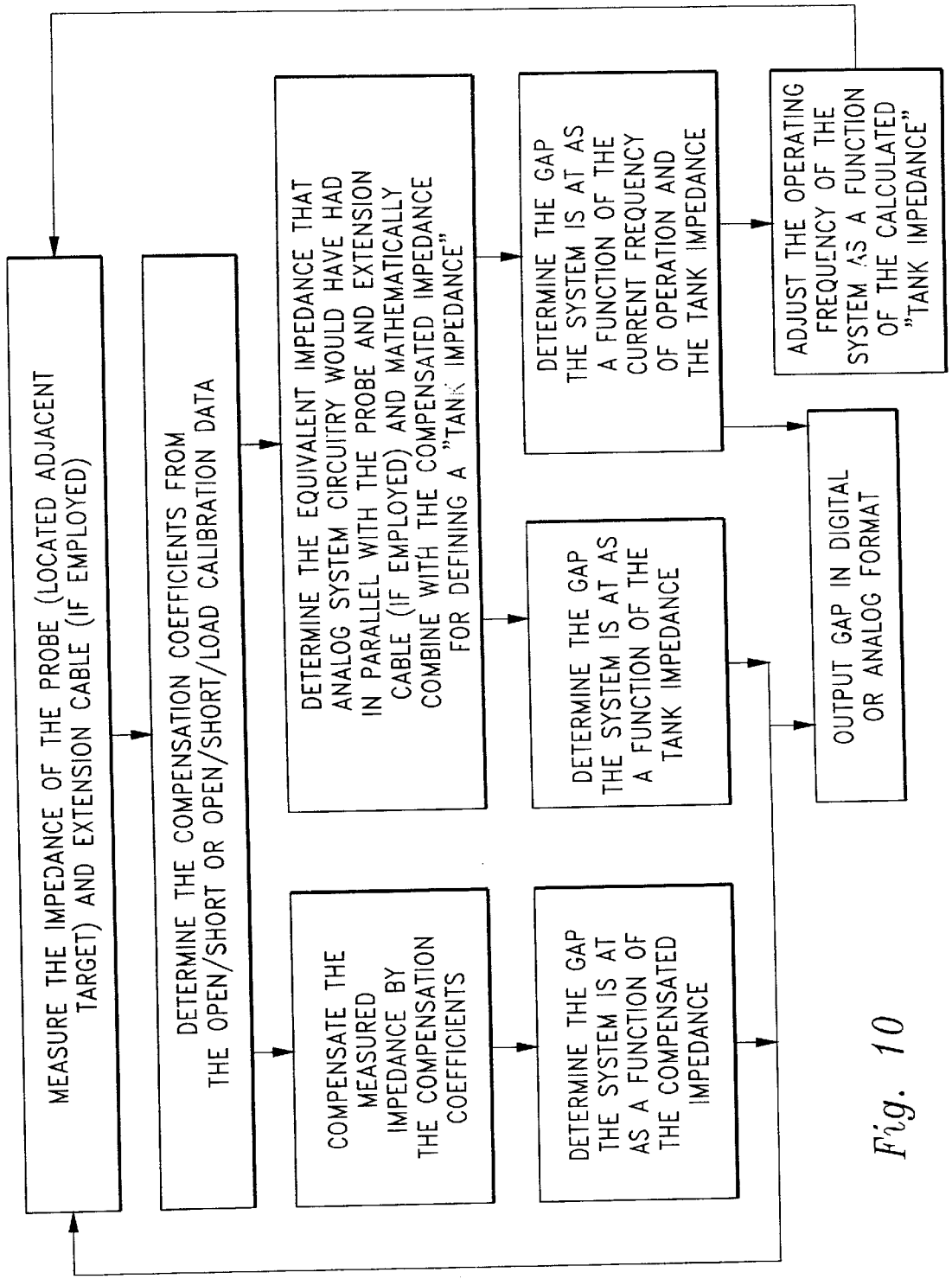
FIG. 10 is a flow chart of a cable compensation and gap measurement method according to the instant invention.

More specifically, and referring to FIG. 10, the resonant method includes measuring the unknown impedance or an uncompensated impedance of the probe located proximate the target T and an extension cable 30 (if employed) as delineated in detail supra. Next, compensation factors or coefficients are determined from open/short or open/short/load calibration tables 125 stored in memory 112 or memory means 120 formed from an open/short or open/short/load calibration or compensation method which will be described in detail infra. The measured impedance is then compensated by using the coefficients determined from the open/short or open/short/load calibration tables 125. The equivalent or load impedance value that the analog proximity circuitry would have had in parallel with the probe and extension cable is mathematically combined with the compensated impedance to form the "tank impedance" of the system 10. As noted hereinabove, the equivalent impedance values can be determined by, for example, using lookup tables 123 of empirically determined values or of mathematically modeled values. The calculated tank impedance is then used to determine the gap the system is at. Alternatively, both the current frequency and the calculated tank impedance can be used to determine the gap the system is at by using one or more mathematical equations 121, one or more look up tables 123, numerical methods 122 or via algorithmic functions 124. Next, the calculated tank impedance can be used to determine the phase shift that would have be needed to be feedback to the oscillator of the analog proximity circuitry so that it heads towards its final steady-state frequency setting. This phase shift can be used to adjust the frequency of the dynamic signal of the system 10 which is driving the probe 12. These steps or a subset of these steps are iteratively repeated to continuously monitor the gap between the probe and the target being monitored.

For example, and referring to FIG. 10, the resonant method can include the steps of measuring the uncompensated impedance of the probe located proximate the target T and an extension cable 30 (if employed) as delineated in detail supra. Then, determining compensation coefficients from the open/short/load calibration tables 125 stored in memory 112 or memory means 120, compensating the measured impedance by using the determined coefficients and determining a gap value as a function of the compensated impedance.

In another example, the unknown impedance of the probe and/or the extension cable can be measured at one fixed frequency to allow for the system 10 to be simplified. The following steps outline one method according to the instant invention for measuring an unknown impedance $Z_{unknown}$ when using a single fixed frequency. The steps include: measuring the uncompensated impedance of the probe and extension cable (if employed); compensating the measured impedance using cable coefficients appropriate for the single fixed frequency; determining a gap value as a function of the compensated measured impedance, and iteratively repeating the measuring, compensating and determining steps to substantially continuously measure the gap between the probe and the target being monitored for providing data correlative to machine status.

The coefficients appropriate for the measured impedance at the fixed single frequency can be empirically predetermined using, for example, the open/short or open/short/load calibration method and then stored in memory 112 or memory means 120 and then later recalled for use with the measured impedance value for determining the gap value as a function of the compensated measured impedance of the probe and/or cable. Furthermore, the equivalent or load impedance that the analog proximity circuitry would have had in parallel with the probe and extension cable can be combined with the compensated impedance and used in determining the gap value as a function of the combined impedance.

Note that each time the gap is measured using, inter alia, the resonant method it can be output in analog or digital form.

The cable calibration or compensation methods referred to supra will now be explored.

In the environment of machine monitoring the unknown impedance measured by the digital proximity system 10 can be that of the extension cable and the proximity probe including the integral sensing element 14 and probe cable 20. The instant invention includes an open/short compensation method and/or an open/short/load compensation method that can be employed for eliminating cable residuals (residual cable impedance and stray cable admittance) of either the extension or probe cable, or both. These two methods and the differences therebetween will be described with the assistance of FIGS. 11 through 14 and then a detailed delineation will be presented on how these methods can be employed for eliminating cable residuals in order to obtain true or compensated probe impedance ($Z_{probe}$) and true or compensated sensing coil impedance ($Z_{sensing\ element}$). These measured impedances or compensated impedances can then be correlated by the system 10 to a gap value by using equations 121, numerical methods 122, algorithmic functions 124 or lookup tables 123 wherein gap values are correlated to measured or compensated impedance values defining the gap or spacing interposed between the probe and the target being monitored. This method of measuring gap can be continuously repeated for monitoring, for example the vibration of a rotating shaft of a machine or an outer race of a rolling element bearing.

Figure 11:
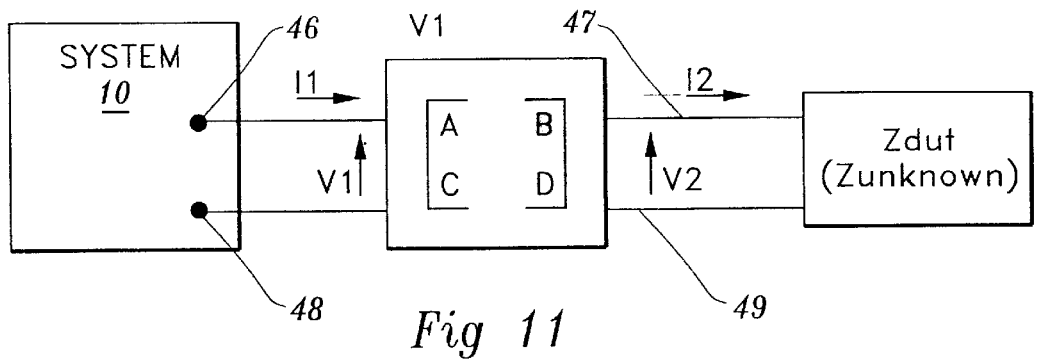
FIG. 11 is a block diagram of an open/short/load compensation model including a four-terminal circuit block according to the instant invention.
Figure 12:
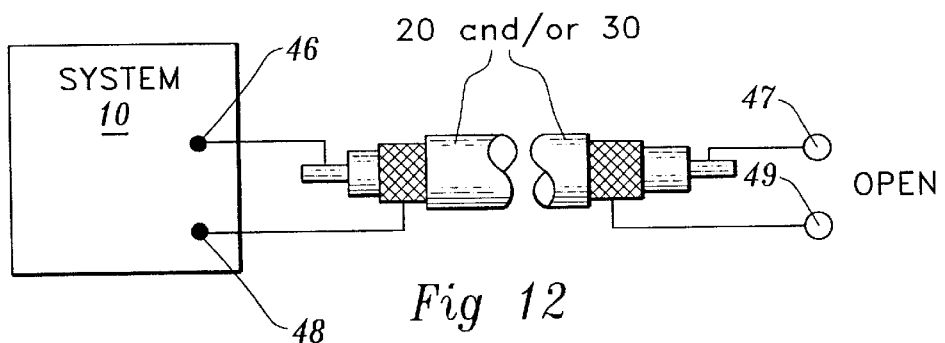
FIG. 12 is a diagram of a cable(s) replacing the four-terminal circuit block shown in FIG. 11 and with the cable(s) in an open condition according to the instant invention.
Figure 13:
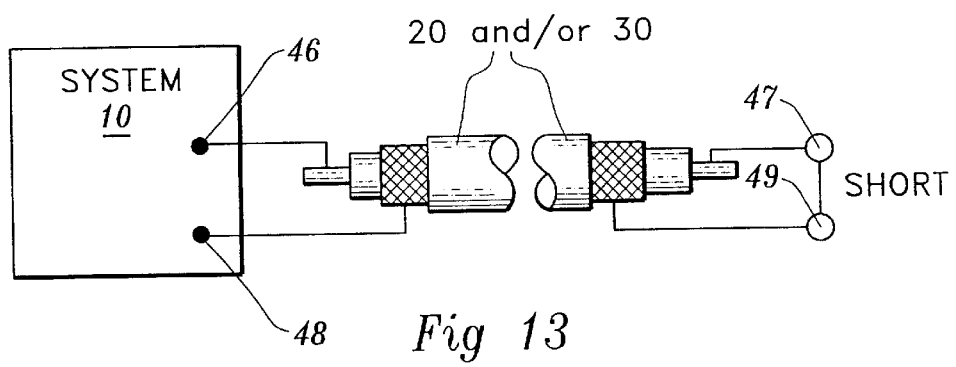
FIG. 13 is a diagram of the cable(s) replacing the four-terminal circuit block shown in FIG. 11 and with the cable(s) in a short condition according to the instant invention.

In general, and referring to FIGS. 11 through 13, the open/short calibration method models the residuals (e.g., residual impedance and stray admittance) as a linear two port or four terminal network represented by ABCD parameters. It should be noted that the open/short calibration method assumes that the network is a symmetrical network. From this restriction, the open/short compensation does not require a load measurement to know each value of the ABCD parameters. Referring to FIG. 11, a theoretical explanation and procedure are as follows:

$$\begin{bmatrix} V_1 \\ I_1 \end{bmatrix} = \begin{bmatrix} A & B \\ C & D \end{bmatrix} \begin{bmatrix} V_2 \\ I_2 \end{bmatrix} = \begin{bmatrix} AV_2 + BI_2 \\ CV_2 + DI_2 \end{bmatrix}$$

therefore;

$$V_1 = AV_2 + BI_2$$

$$I_1 = CV_2 + DI_2$$

thus, the measured impedance Z is represented as:

$$Z = \frac{V_1}{I_1} = \frac{AV_2 + BI_2}{CV_2 + DI_2} \qquad \text{(equation 1)}.$$

Open measurement: when the unknown terminals 47, 49 are opened, $I_2=0$. Then, from equation 1, the measured impedance $Z_{OM}$ is:

$$Z_{OM} = A/C \qquad \text{(equation 2)}.$$

Short measurement: when the unknown terminals 47, 49 are shorted, $V_2=0$. Then, from equation 1, measured impedance $Z_S$ is:

$$Z_S = B/D \qquad \text{(equation 3)}.$$

A limited condition for the ABCD parameters is as follows: when the unknown network is "symmetric" A=D (equation 4). Thus, a symmetrical network can be defined as one where the parameters A and D are equal to one another.

DUT (Device Under Test) measurement: when the DUT is connected to terminals 47, 49, its impedance value is represented as $$Z_X = V_2/I_2 \qquad \text{(equation 5)}.$$

From equations 1 and 5, its measured impedance value $Z_{XM}$ is:

$$Z_{XM} = \frac{V_1}{I_1} = \frac{AV_2 + BI_2}{CV_2 + DI_2} = \frac{\frac{AV_2}{I_2} + B}{\frac{CV_2}{I_2} + D} = \frac{AZ_X + B}{CZ_X + D} \quad \text{equation 6.}$$

Equation 6 can be solved for $Z_X$ and from equations 2 and 3, A and B are erased to give:

$$Z_X = \frac{D}{C} \frac{Z_S - Z_{XM}}{Z_{XM} - Z_{OM}} \quad \text{equation 7.}$$

From equations 2 and 4, unknown parameters C and D in equation 7 can be erased and then the true or compensated value of the unknown impedance of the DUT can be defined as $Z_X$ which is determined by an open/short equation which is as follows:

$$Z_X = Z_{OM} \frac{Z_S - Z_{XM}}{Z_{XM} - Z_{OM}} \quad \text{equation 8}$$

wherein:

$Z_{OM}$ is the measured open impedance $Z_S$ is the measured short impedance $Z_{XM}$ is the measured value of the unknown impedance $Z_{unknown}$ of the DUT Note: all values are complex numbers.

In general, the system 10 can employ the open/short method as follows. First, the impedance of the probe cable 20, the extension cable 30 or both coupled together is measured with one end left opened (FIG. 12) for defining $Z_{OM}$. Second, the impedance of the probe cable 20, the extension cable 30 or both coupled together is measured by shorting the one end (FIG. 13) for defining $Z_S$. Third, an unknown impedance is coupled to the probe cable 20, the extension cable 30 or both and its measured impedance $Z_{XM}$ is obtained by preferable using the voltage ratio apparatus and method of the system 10 as delineated supra wherein $Z_{XM}$ is the $Z_{unknown}$ described hereinabove. Finally, the true or compensated value $Z_X$ of the measured unknown impedance is determined from the open/short equation $$Z_X = Z_{OM}*(Z_S - Z_{XM})/(Z_{XM} - Z_{OM}).$$

For example, the true or compensated value of the impedance of the proximity probe 12 coupled to the system 10 via the extension cable 30 can be calculated from the following equation:

$$Z_X = Z_{OM}*(Z_S - Z_{XM})/(Z_{XM} - Z_{OM})$$

wherein:

$Z_{OM}$ and $Z_S$ are respectively, the measured open and short impedances utilizing only the extension cable 30, $Z_{XM}$ is the measured impedance of the proximity probe 12 coupled to the extension cable 30 which in turn is coupled to the system 10 (Note that in this example $Z_{XM}$ is the $Z_{unknown}$ described supra with the extension cable employed), and $Z_X$ is the true or compensated impedance value of the proximity probe 12 wherein the residuals of the extension cable 30 are eliminated.

Thus, the extension cable residuals are mathematically eliminated by using the compensation coefficients $Z_{OM}$, $Z_S$ and $Z_{XM}$ to define the compensated proximity probe impedance of the proximity probe 12.

Likewise, $Z_{OM}$ and $Z_S$ can be respectively, the measured open and short impedances utilizing only the probe cable 20 and $Z_{XM}$ can be the measured impedance of the sensing element 14 coupled to the probe cable 20 which in turn is coupled to the system 10. Thus, $Z_X$ would then be the true or compensated value of the sensing element 14 with the residuals of probe cable 20 eliminated.

Additionally, $Z_{OM}$ and $Z_S$ can be respectively, the measured open and short impedances utilizing both the probe cable 20 and the extension cable 30 coupled together and $Z_{XM}$ can be the measured impedance of the sensing element 14 coupled to the probe cable 20 which in turn is coupled to the system 10 via the extension cable 30. Thus, $Z_X$ would then be the true or compensated value of the sensing element 14 with the residuals of both the probe cable 20 and the extension cable 30 eliminated.

Thus, the residuals of the probe cable 20, the extension cable 30 or both coupled together can be mathematically eliminated by using the compensation coefficients $Z_{OM}$, $Z_S$ and $Z_{XM}$ to define the compensated proximity probe impedance of the proximity probe 12 or the compensated sensing element impedance of the sensing element 14.

Furthermore, true impedance values or compensation coefficients for different extension or probe cable configurations including different lengths can be stored in memory, for example, memory means 120 as look up or calibration tables 125 and recalled when necessary. For example, the system 10 can measure the impedance of the serial coupling of the extension cable 30 and proximity probe 12 and then eliminate via impedance values or compensation coefficients the extension cable impedance to determine the proximity probe impedance or eliminate via impedance values or compensation coefficients both the extension cable impedance and probe cable impedance to determine the sensing element or coil impedance. Likewise, the system 10 can measure the impedance of the proximity probe 12 and then eliminate via impedance values or compensation coefficients the probe cable impedance to determine the sensing element or coil impedance.

The following three methods can be used to determine the values for $Z_{OM}$ and $Z_S$. First, a tuned cable length is used where the length is set so that they most closely match known compensation values stored in the memory means of the system 10. Second, a user installs the extension cable to an input of the system 10 and then performs the open/short compensation method as described above and then stores the measured values in the memory means 120. Third, by mathematically determining the cable length and compensation values and using these values to eliminate cable residuals.

The DDS devices of the system 10 can be used for generating the drive signal by loading digital control signals from the DSP into the DDS and letting the DDS drive the probe cable 20, the extension cable 30 or both with arbitrary waveforms at whatever frequency is needed.

The open/short/load compensation is an advanced compensation technique that is applicable to complicated residual circuits and is the preferred cable calibration or compensation method according to the instant invention. To perform open/short/load compensation, three measurements are required before measuring a DUT (e.g., the unknown impedance of the probe monitoring a metallic target object). These measurements include a measurement with the unknown terminals 47, 49 open, a measurement with the unknown terminals 47, 49 shorted and a measurement with a standard DUT (load) having a known value coupled between the unknown terminals 47, 49.

The open/short/load compensation method is particularly useful when the extension cable 30 is used whose length cannot be compensated with a cable length correction function nor be minimized with the open/short correction method described above.

The open/short/load correction requires the measurement data of at least one standard DUT having a known value in addition to the open/short measurement data. Similarly to the open/short method, and referring to FIG. 11, the open/short/load compensation method models the residuals as a four-terminal network circuit represented by the ABCD parameters. Each parameter is known if three conditions are known and if the four-terminal network is a linear circuit.

From FIG. 11, $Z_1 = V_1/I_1$, $Z_2 = V_2/I_2$ and $$Z_1 = \frac{AV_2 + BI_2}{CV_2 + DI_2} = \frac{AZ_2 + B}{CZ_2 + D}$$

The parameters A, B, C and D can be removed when using the following definitions:

$Z_O$ is the measured open impedance with the terminals 47, 49 open, $Z_S$ is the measured short impedance with the terminals 47, 49 closed, $Z_{SM}$ is the measured impedance of the standard DUT when connected to the terminals 47, 49, $Z_{std}$ is the true (or expected) value of the standard DUT, $Z_{XM}$ is the measured value of the DUT having the unknown impedance and connected to the terminals 47, 49 (for example, the proximity probe 12)

$Z_{DUT}$ is the true or compensated value of the DUT having the unknown impedance (for example, the compensated impedance of the proximity probe 12).

The true or compensated value of the unknown impedance $Z_{DUT}$ is determined by an open/short/load equation which is as follows:

$$Z_{DUT} = \frac{Z_{std}(Z_O - Z_{SM})(Z_{XM} - Z_S)}{(Z_{SM} - Z_S)(Z_O - Z_{XM})}$$

Note: all values are complex numbers.

Figure 14:
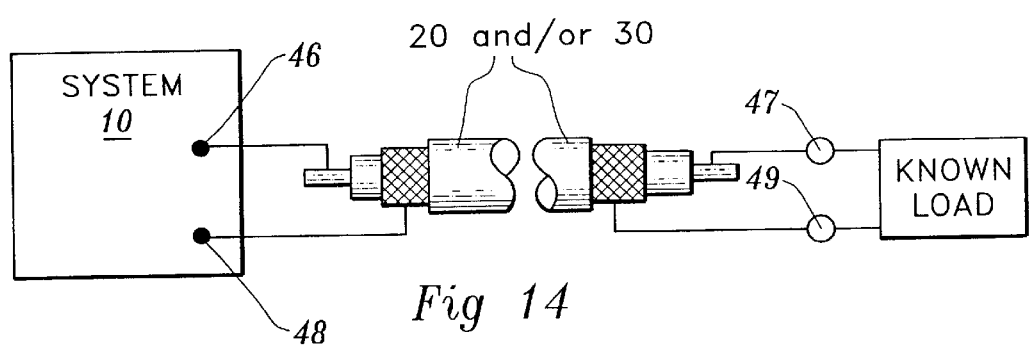
FIG. 14 is a diagram of the cable(s) replacing the four-terminal circuit block shown in FIG. 11 and with the cable(s) coupled to a load according to the instant invention.

Thus, in general, the system 10 can employ the open/short/load method as follows. First, an impedance of the probe cable 20, the extension cable 30 or both cables coupled together is measured with one end left opened (FIG. 12) and is defined as $Z_O$. Second, an impedance of the probe cable 20, the extension cable 30 or both cables coupled together is measured by shorting the one end (FIG. 13) and is defined as $Z_S$. Third, $Z_{SM}$ is defined as impedance which is measured with a known load (a standard DUT or load) coupled to one end of the probe cable 20, to one end of the extension cable 30 or to one end of coupled cables (FIG. 14). Fourth, an impedance is coupled to the probe cable 20, to the extension cable 30 or to the combination of coupled cables and its impedance is measured using the voltage ratio apparatus and method of the system 10 as delineated hereinabove for defining $Z_{XM}$. Finally, the true or compensated impedance of $Z_{XM}$ is then calculated from the open/short/load equation delineated hereinabove.

For example, the system 10 can employ the open/short/load method as follows. First, an impedance of the extension cable 30 is measured with one end left opened (FIG. 12) for defining $Z_O$. Second, an impedance of the extension cable is measured by shorting the one end (FIG. 13) for defining $Z_S$. Third, an impedance of the extension cable is measured with one end coupled to a known load (a standard DUT or load) as shown in FIG. 14 for defining $Z_{SM}$. Fourth, the system 10 is coupled to the extension cable 30 which in turn is coupled to the proximity probe 12 for measuring $Z_{XM}$. Note that $Z_{XM}$ is the same measurement as that of the measurement of the unknown impedance $Z_{unknown}$ delineated supra with the extension cable employed. Finally, the true proximity probe impedance ($Z_{probe}$) can then be calculated from the open/short/load equation as follows:

$$Z_{probe} = \frac{Z_{std}(Z_O - Z_{SM})(Z_{XM} - Z_S)}{(Z_{SM} - Z_S)(Z_O - Z_{XM})}$$

where:

$Z_O$ is the measured open impedance of the extension cable 30 (FIG. 12), $Z_S$ is the measured short impedance of the extension cable 30 (FIG. 13), $Z_{SM}$ is the measured impedance of the load (standard load or standard DUT) coupled to the extension cable 30 in place of the proximity probe 12 (FIG. 14), $Z_{std}$ is the known value of the load impedance (standard load or standard DUT), $Z_{XM}$ is the measured impedance of the probe 12 coupled to the extension cable 30, $Z_{probe}$ is the true or compensated complex electrical impedance of the proximity probe 12 with the residuals of the extension cable eliminated.

Likewise, $Z_O$ and $Z_S$ can be respectively, the measured open and short impedances utilizing only the probe cable 20. The impedance of the probe cable can then be measured with a standard load coupled to one end to define $Z_{SM}$. Next, an impedance of the probe cable can be measured with the sensing element or coil 14 coupled to one end to define $Z_{XM}$. Note that $Z_{XM}$ is the same measurement as that of the measurement of the unknown impedance $Z_{unknown}$ of the proximity probe 12 delineated supra without the extension cable 30 employed. Finally, the true or compensated sensing element impedance ($Z_{sensing\ element}$) can then be calculated from the open/short/load equation with the residuals of probe cable 20 eliminated.

Additionally, $Z_O$ and $Z_S$ can be respectively, the measured open and short impedances utilizing both the probe cable 20 and the extension cable 30 coupled to one another and then, the impedance of the coupled probe cable 20 and extension cable 30 is measured with a standard load coupled to the end of the probe cable 20 to define $Z_{SM}$. Next, the impedance $Z_{XM}$ can be determined by measuring the impedance of the extension cable 30 coupled to the probe cable 20 which in turn is coupled to the sensing element or coil 14. Thus $Z_{XM}$ is the measurement of the unknown impedance $Z_{unknown}$ as delineated supra with the extension cable 30 employed. Finally, the true or compensated sensing element impedance ($Z_{sensing\ element}$) can then be calculated from the open/short/load equation with residuals of both the probe cable 20 and the extension cable 30 eliminated.

One specific method of canceling out the effects of an added extension cable during the digital impedance measurement by the system 10 using the open/short/load compensation method is as follows:

1. A user cuts an extension cable 30 to the length that is most beneficial for the mechanical installation of the proximity probe 12 and installs a connector on the trimmed end.
2. The user connects the trimmed extension cable 30 to the system 10 at nodes 46, 48 with the probe end open.

3. The user performs an open/short/load calibration at terminals 47, 49 as described above on the trimmed extension cable 30 and the data is either manually or automatically stored in, for example, memory 120.
4. The user connects the proximity probe 12, for example, a 0.5 or 1.0 meter proximity probe 12 to the trimmed extension cable via connectors.
5. The system 10 than measures the impedance and mathematically eliminates the residuals of the trimmed extension cable as described supra. The residual impedance is that of the probe 12. Thus, the system 10 is calibrated to operate with the proximity probe 12 and outputs a linearized gap signal.

In another embodiment the system can employ a load/load/load method as follows. First, an impedance $Z_{L1}$ of the extension cable is measured with one end coupled to a first load. Second, an impedance $Z_{L2}$ of the extension cable is measured with one end coupled to a second load. Third, an impedance $Z_{L3}$ of the extension cable is measured with one end coupled to a third load. Fourth, an impedance $Z_{XM}$ is measured by the system 10 wherein the extension cable is coupled between the digital proximity system 10 and the proximity probe 12 and thus the system measures the impedance of both the proximity probe 12 and the extension cable 30. Finally, the true or compensated probe impedance ($Z_{probe}$) can then be calculated from the following equation:

$$Z_{probe} = \frac{Z_{std}(Z_{L1} - Z_{L3})(Z_{XM} - Z_{L2})}{(Z_{L3} - Z_{L2})(Z_{L1} - Z_{XM})}$$

wherein:

$Z_{L1}$ is the measured impedance of the extension cable 30 coupled to a first load, $Z_{L2}$ is the measured impedance of the extension cable 30 coupled to a second load, $Z_{L3}$ is the measured impedance of the extension cable 30 coupled to a third load (standard load or standard DUT), $Z_{std}$ is the known value of the third load impedance (standard load or standard DUT), $Z_{XM}$ is the measured impedance of the coupled probe 12 and extension cable 30, $Z_{probe}$ is the compensated complex electrical impedance of the proximity probe 12.

Thus, the proximity probe impedance of the proximity probe is calculated as a function of the measured impedance, the first load impedance, the second load impedance, and the third load impedance for compensating for extension cable residuals. The proximity probe impedance is then correlated to a gap between the proximity probe and the conductive target material.

Preferably, the second load has an impedance that is less than the impedance of the first load and the third load has an impedance that is less than the impedance of the first load and greater than the impedance of the second load.

Additionally, note that this method can also be used to determine the true value of the sensing element wherein $Z_{L1}$, $Z_{L2}$, $Z_{L3}$ respectively replace $Z_O$, $Z_S$ and $Z_{SM}$.

It should also be noted that the following conditions may be required for the open/short and/or the open/short/load methods. First, when getting the open correction data, the distance between measurement terminals should be the same as the distance that is required for actually holding the DUT. Secondly, when getting the short correction data, the measurement terminals should be shorted or connected to a shorting device and the residual impedance should be less than the impedance value of the DUT. Thirdly, when selecting a standard DUT (load) for the load correction step there is no restriction that an inductor must be used for inductance measurement, or capacitor must be used for a capacitance measurement. Any device can be used if its impedance value is accurately known. It is important to use a stable standard DUT not susceptible to influences of environment such as temperature or magnetic fields. From this viewpoint, capacitors or resistors are better suited than inductors which are more susceptible to the environment. When measuring a DUT's various impedance values, a 100 to 1,000 ohm resistor standard DUT (load) may provide the best results. When measuring a DUT of one impedance value, a standard DUT (load) having approximately the same impedance as that of the DUT to be measured may provide the best results. A 100 to 1,000 ohm resistor standard DUT (load) may provide the best results for a DUT having an unknown impedance which is either very high or very low.

A standard DUT (load) may be measured using a direct connection to nodes 46, 48 of the system 10 after performing the open/short correction method at nodes 46, 48 to determine compensation coefficients to be used in calculating the value of the standard load using equation eight (8) as delineated hereinabove. Additionally, It should be noted that the open/short/load compensation method may be required to employ a stable known load which is measured in the same way that the DUT will be measured and is of the same approximate value.

In conclusion, the system 10 can be calibrated at nodes 46, 48 by using the open/short/load method thereby defining a first calibration plane at nodes 46, 48 and including in memory 120 a correction or compensation function or table of the internal impedance of the system. For example, the calibration tables 125 can include a correction function or compensation including compensation coefficients which compensate for the resistance means 40 such that only the ratio $V_{2C}/(V_{1C}-V_{2C})$ of the complex voltages is required to determine the unknown impedance value $Z_{unknown}$ of the probe 12. Additionally, when an extension cable is coupled to nodes 46, 48 the system 10 can be calibrated at the end 36 of the extension cable 30 by using the open/short/load method thereby defining a second calibration plane. Thus, the calibration tables 125 can include a correction or compensation function which compensates for the extension cable such that the ratio $V_{2C}/(V_{1C}-V_{2C})$ of the complex voltages is correlative to unknown impedance value $Z_{unknown}$ of the probe 12 and not the extension cable 30 and probe 12 combination.

Additionally, the system 10 can be used to make all of the above delineated impedance measurements for the open/short method, the open/short/load method and the load/load/load method and store these values in memory.

Referring to FIGS. 16 through 22, the digital proximity system 10 further includes a unique material identification and calibration method, a unique material insensitivity method, and a unique inductive ratio method.

Figure 15:
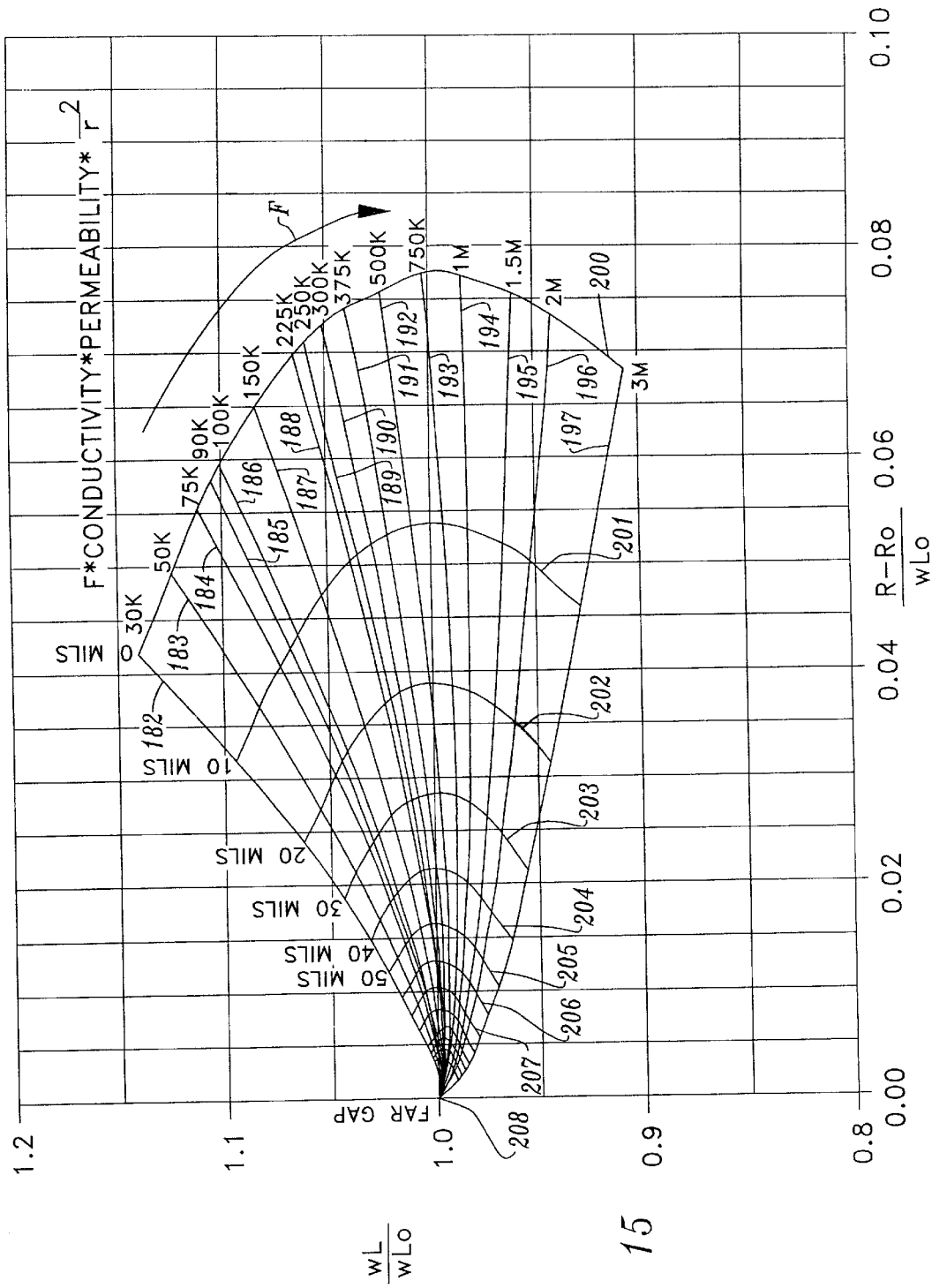
FIG. 15 is an exemplary graph showing a normalized impedance diagram.

In order to understand how these unique methods work, one must first understand a "Normalized Impedance Diagram". Referring to FIG. 15, a normalized impedance diagram is shown and is comprised of a multiplicity of normalized impedance curves. This graph can be generated by taking a proximity probe and measuring its impedance at different frequencies and at different gaps from, for example, a standard E 4140 steel target. The lines 182 through 197 radiating outward (from the (0.0, 1.0) points) are gap lines. They represent the normalized impedance due to the target at a constant frequency as the gap is changed from very close (the rightmost ends of the lines) to the farthest gap (the 0.0, 1.0 point). These lines rotate clockwise along arrow F as the frequency is increased. The arcs 200 through 208 represent the impedance of the probe located at a fixed gap as the frequency varies.

The method of obtaining this basic normalization is as follows:

1. Measure a far gap impedance of the probe: Far gap impedance=$R_o$+$jwL_o$.
2. Measure an impedance of the probe near the target: Near gap impedance=R+jwL.
3. Determine a normalized impedance which is comprised of a normalized resistance term and a normalized reactance term as follows:
Normalized resistance=$(R-R_o)/wL_o$ and
Normalized reactance=$wL/wL_o$.
4. Plot each point on a graph and connect the points done at the same frequency.
5. Connect the points done at the same gap thereby obtaining a graph as shown in FIG. 10.

Each target has its own characteristic normalized impedance diagram and it has been observed that the curves rotate clockwise as the conductivity and permeability of the target increase. Also, it has been observed that there is much more reactive change with gap than there is a resistive change as the conductivity and permeability of the target increase. The prior art systems are much more sensitive to resistance changes than to reactive changes which makes the prior art systems more difficult to calibrate for high conductivity materials as a result of there not being much resistance change to detect.

Note that the basic normalization method can be followed to measure the far gap and the near gap impedance of the probe in combination with the extension cable to obtain a "Normalized Impedance Diagram" of the probe/extension cable combination.

Additionally, one or more normalized impedance curves can be generated by taking a probe and measuring its impedance at different frequencies and different gaps with different target materials and storing this information in, for example, the memory means 120.

Now with the basic normalization method in mind, the unique material identification and calibration method, the unique material insensitivity method and the unique inductive ratio method will be delineated in detail according to the instant invention.

Figure 16:
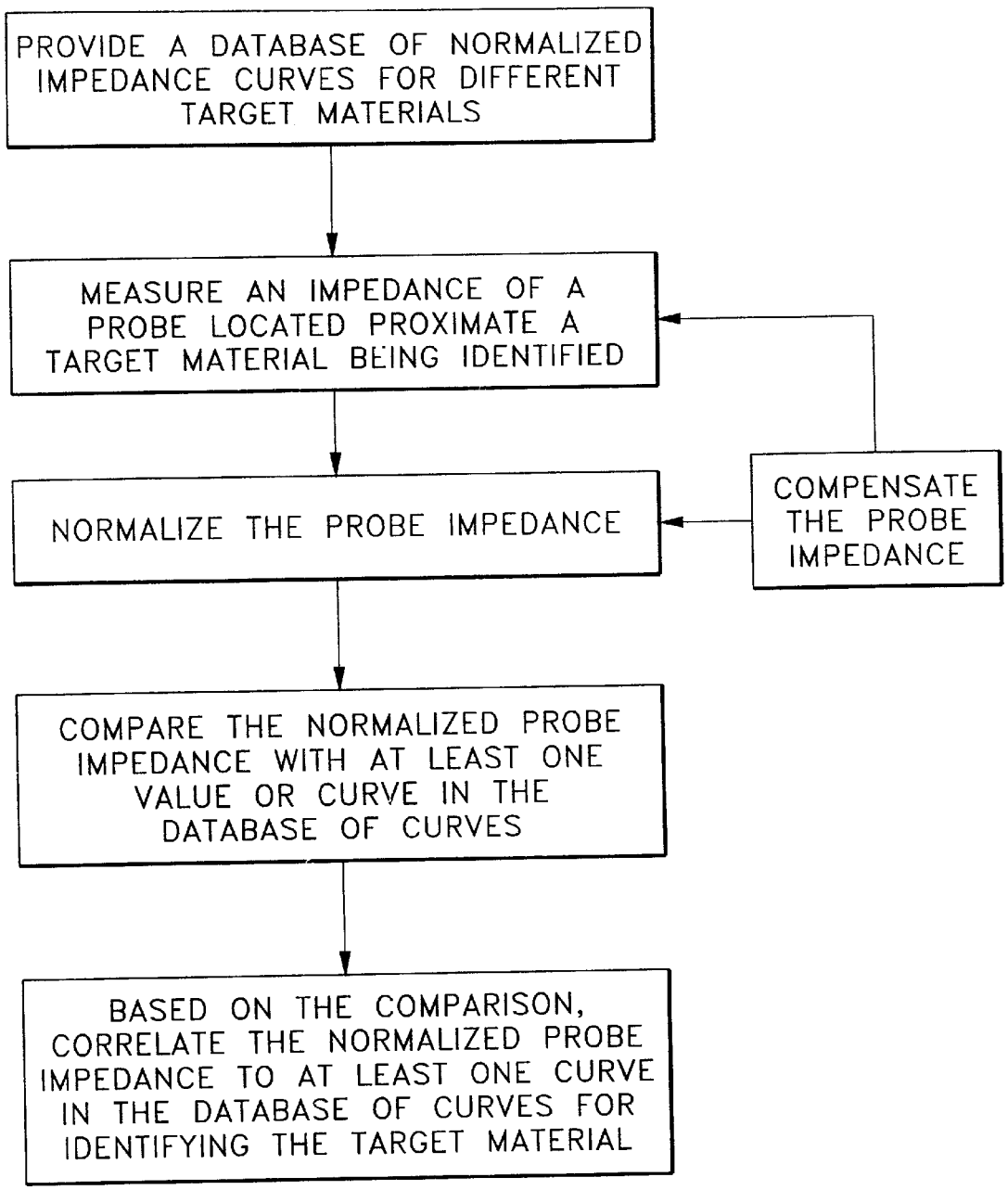
FIG. 16 is a flow chart of the material identification and calibration method according to the instant invention.
Figure 17:
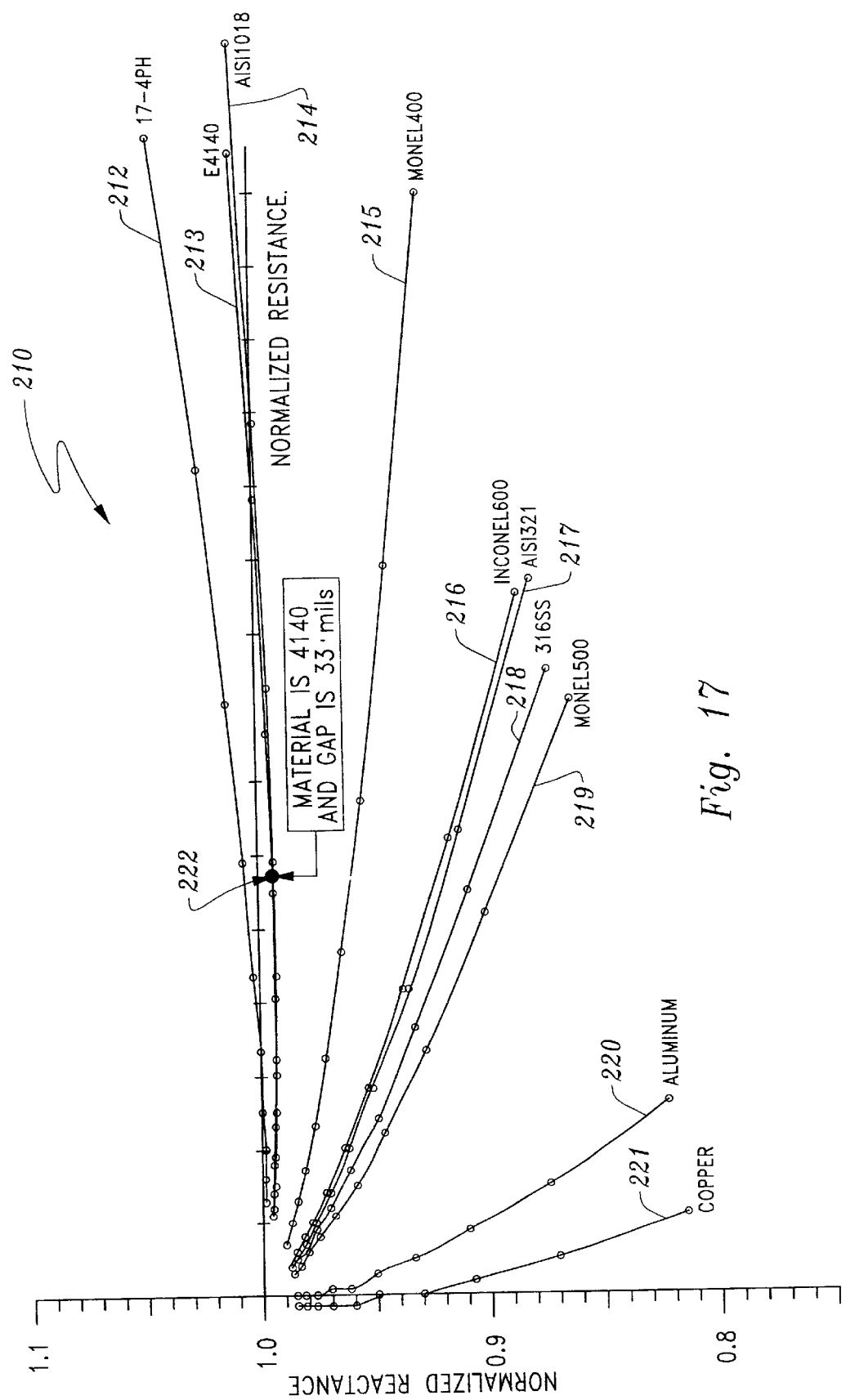
FIG. 17 is an exemplary graph showing normalized impedances of different materials, which is employed in the material identification and calibration method according to the instant invention.

Referring to FIGS. 16 and 17, the unique material identification and automatic calibration method of the instant invention allows the system 10 to identify a material that the system 10 is monitoring and to automatically calibrate the system 10 for that material.

More specifically, and referring to FIG. 16, the material identification and automatic calibration method of the digital proximity system 10 includes the following steps. At the outset, the probe of the digital proximity system 10 is located proximate the target material to be identified and the system 10 measures the impedance of the probe as delineated in detail supra. The system 10 then determines the normalized impedance value of the probe by using this measured impedance which may be compensated according to the instant invention and the far gap impedance of the probe which, for example, can be manually entered via input means 148 or called up from memory means 120. Next, the normalized impedance value can be correlated to a point or impedance on a previously stored normalized curve for a specific target material and probe type combination. Once the correlation is found, the material of the target can be identified. Alternatively, a user can enter the material type into the system 10 via an input means 148 which would then correlate a stored normalized curve to the specific target material and probe type combination.

Note a multiplicity of normalized impedance curves for a multiplicity of different targets and probe types may be stored in the memory means 120 as, for example, material identification tables 126. These tables can then be accessed at any time by the system 10 for identifying the material the probe is monitoring and performing the self calibration process based on the identified material. These curves can be previously generated by taking one or more probes and measuring their impedance values at different frequencies and different gaps with different target materials and storing this information in, for example, the table 126 of the memory means 120.

Additionally, the memory means 120 can include calibration data 134 which includes the parameters necessary for automatically calibrating the system 10 for the identified material. Therefore, once the material of the target is identified, the digital proximity system 10 can pull the appropriate system calibration data out of the memory means 120 for automatically calibrating the system 10 for the identified material and thus, generating gap data for monitoring the identified material.

FIG. 17 shows an example of a normalized impedance diagram 210 which reflects normalized impedance curves for the same probe running at a single frequency, but looking at multiple targets. Each line 212 through 220 radiating outward from the (0.0, 1.0) point represents the normalized impedance of different target materials at the constant frequency as the gap is changed from very close (the rightmost end of the line) to the farthest gap (the 0.0, 1.0 point). This information can be stored in memory 120 and the material identification and automatic calibration method can be used to determine point 222 and correlate the point to a normalized curve of a 4140 type of material. This information can then be used to determine the calibration parameters from the calibration data stored in the memory 120 for automatically calibrating the system 10 and generating, for this example, a gap of 33 mils.

Note that the aforementioned material identification and automatic calibration method can be followed with the probe being replaced with the probe/extension cable combination to obtain a normalized impedance value which is correlated to a point on a previously stored normalized curve for a specific target material. Once the correlation is found, the material of the target can be identified.

This method has the huge advantage of being backwards compatible with analog proximity systems.

As mentioned hereinabove, and referring to FIGS. 16 and 17, the unique material identification method of the instant invention allows the system 10 to identify a material located proximate the proximity probe 20.

In one form, the system 10 digitally measures the complex impedance of the probe 20 disposed adjacent one or more different yet known target materials and driven at one or more different frequencies. The system 10 then calculates a normalized impedance curve for each different target material at each different frequency and stores these curves as an equation, as an algorithmic function or as a database of values in a memory, for example, memory means 120. Thereafter, the system 10 subsequently identifies unknown materials by first digitally measuring the complex impedance of the probe 20 driven at one or more different frequencies and disposed adjacent an unknown material. Next, the system 10 calculates the normalized impedance curve for the unknown material at the one or more different frequencies by using an equation an algorithmic function or a database of values for the unknown material at each driving frequency. The system 10 then compares the equation (or algorithm) determined for the unknown material to one or more previously determined equations (or algorithms) for known materials to obtain or interpolate a match for identifying the unknown material. Alternatively, the system 10 compares one or more values in the database of values for the unknown material at each driving frequency to one or more values in one or more previously determined databases of known materials to obtain or interpolate a match for identifying the unknown material. Note that all measured impedances can be compensated by using the open/short or open/short/load compensation methods according to the instant invention prior to the probe or coil impedance being normalized.

In a second form, the system 10 identifies a unknown material by depending primarily on the curve shape of the normalized impedance response and the angle of the vector the normalized impedance response sweeps out from the normalized resistance value 0.0 and the normalized reactance value 1.0 to the actual normalized impedance value of the target at any particular frequency. Thus, material identification is not based on the absolute position of any normalized impedance reading and as a result, lines do not have to overlap to indicate the same material characteristics. Variations in "liftoff" or separation between the probe and the target may cause variations in the absolute position of the normalized impedance measurement, but will not affect its curve or angular relationship with the origin.

When different materials have very similar conductivity the system 10 can measure the impedance characteristics of each target at two or more different gaps to determine the "liftoff line" for each material. This assists in identifying the relative position of the material's normalized impedance response when plotted on a graph.

The system 10 can utilize these forms alone or in combination with the material identification and automatic calibration method for monitoring rotating and reciprocating machinery as explained hereinabove and with reference to FIGS. 16 and 17.

Another use of the material identification methods or forms according to the instant invention is in the area of identifying and/or sorting coins and precious metals. For example, the system 10 can determine the normalized impedance of a series of coins and/or precious metals (targets) placed adjacent the probe 12. The normalized impedance values can be recorded at several different frequencies. These values can then be compared or plotted with known standards 123 of coins and/or precious metals for material identification and discrimination.

Material discrimination is based primarily on the curve shape of the normalized impedance response and the angle of the vector the normalized impedance response sweeps out from the normalized resistance value 0.0 and the normalized reactance value 1.0 to the actual normalized impedance value of the target(s) at any particular frequency. Thus, material discrimination is not based on the absolute position of any normalized impedance reading and as a result, normalized curves do not have to overlap to indicate the same material characteristics. Variations in "liftoff" or distance between the probe and any target may cause variations in the absolute position of the normalized impedance measurement, but will not affect its curve or angular relationship with the origin.

When different materials have very similar conductivity the system 10 can measure the impedance characteristics of each target at two different gaps to determine the "liftoff line" for each material. This assists in identifying the relative position of the material's normalized impedance response when, for example, plotted on a graph.

One empirical example of the discrimination method delineated above used the system 10 to preform eddy current analysis on different metal and coin types. The system 10 measured the impedance of the different metal and coin types, normalized these impedances and plotted the results. It was shown that a curve shape of the normalized impedance response and an angle of the vector or curve shape of the normalized impedance response that sweeps out from the normalized resistance value 0.0 and the normalized reactance value 1.0 for gold, gold coins, silver, silver coins and copper-nickel silver dollars was such that the discrimination of one from the other was easily discernable with a single impedance measurement. These materials were also easily discriminated against platinum and palladium.

In the case of distinguishing between platinum and palladium, different materials having very similar conductivity, the system 10 measured the impedance characteristics of each target at two different gaps to determine the "liftoff line" for each material. This assisted in identifying the relative position of the material's normalized impedance response when, for example, plotted on a graph.

Figure 18:
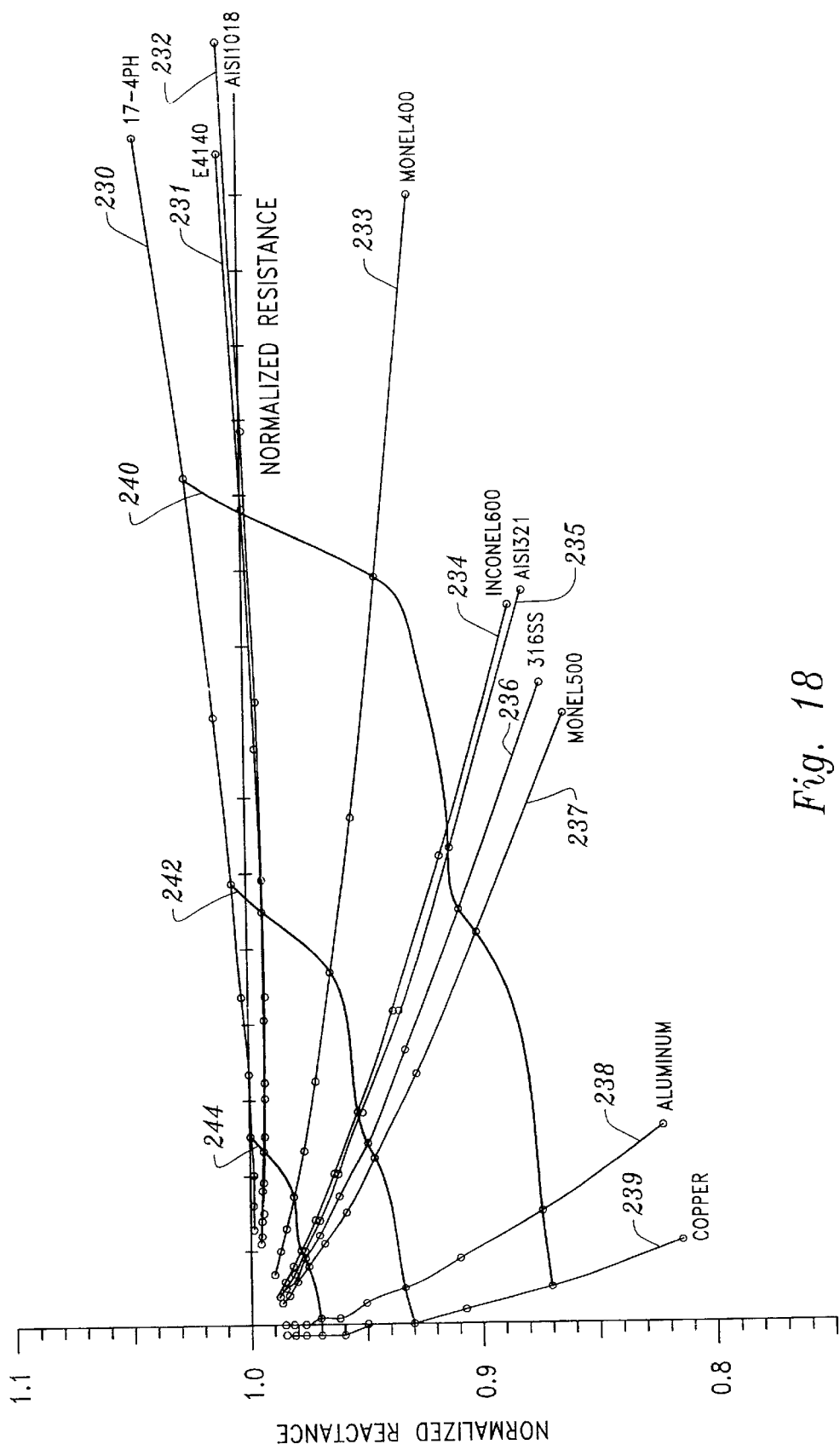
FIG. 18 is an exemplary graph showing normalized impedances of different materials and showing a series of gap locus employed by the material insensitive method according to the instant invention.
Figure 19:
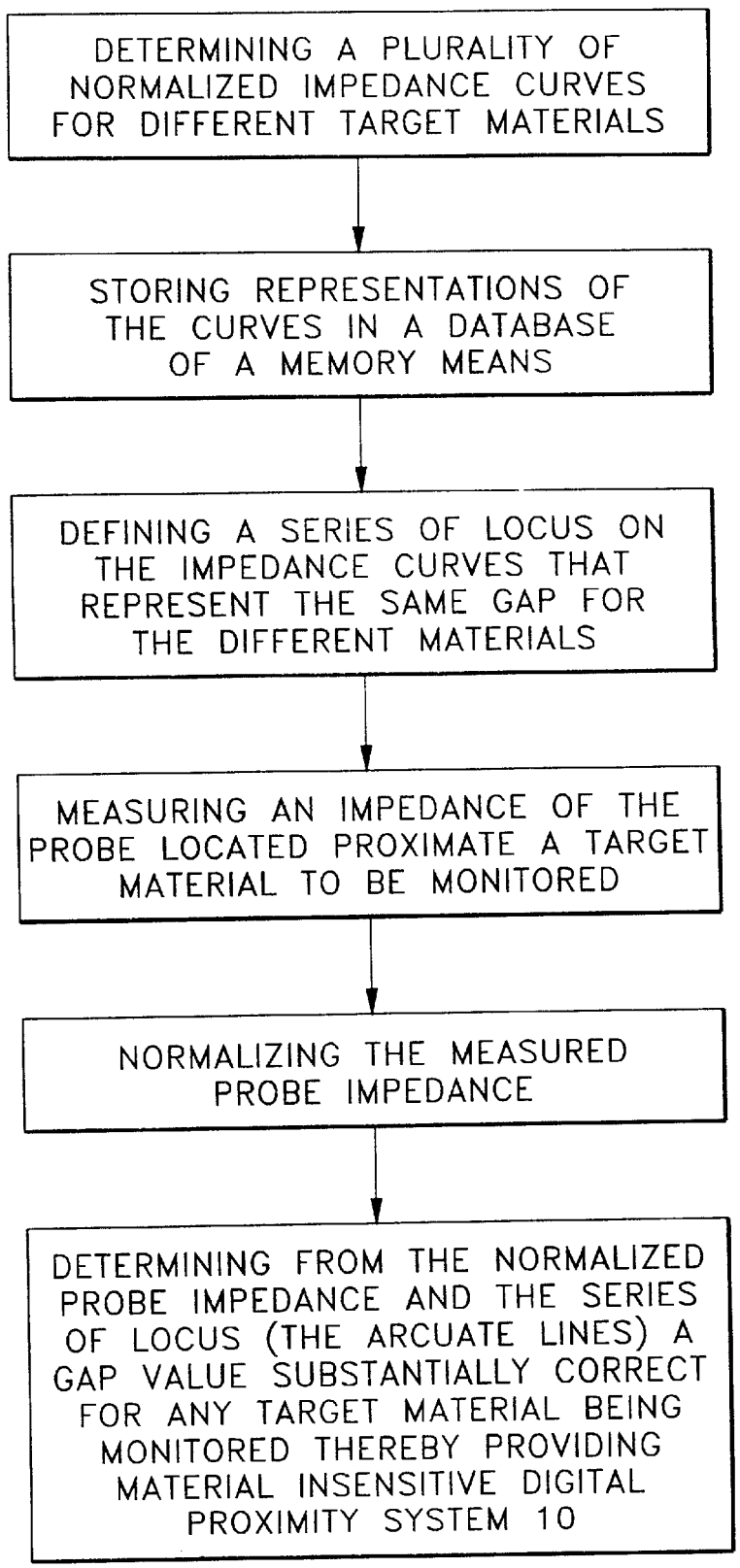
FIG. 19 is a flow chart of the material insensitive method according to the instant invention.

Referring to FIGS. 18 and 19, The unique material insensitive method of the instant invention allows the system 10 to monitor different target materials without having to be re-calibrated for each different material thereby providing a material insensitive digital proximity system 10.

More specifically, and referring to FIGS. 18, a graph is shown of a normalized impedance diagram for the system 10 running at a single frequency, but looking at multiple targets. Each line (230 through 238) radiating outward from the (0.0, 1.0) point represents the normalized impedance of different target materials at a constant frequency as the gap is changed from very close (the rightmost end of the line) to the farthest gap (the 0.0, 1.0 point). These lines rotate clockwise as the conductivity and permeability of the target increase. The arcuate lines 240, 242 and 244 are a series of locus which connect the points on each line (230 through 238) that are at the same gap. One or more normalized impedance curves each including a series of locus can be generated by taking a probe and measuring its impedance at different frequencies and different gaps with different target materials and storing this information in, for example, a database or table(s) 128 of the memory means 120. Each locus can be represented by an equation(s) 129 or numerical methods 130 which approximate the arcuate lines of constant gap. Thus, the system 10 is designed so that any impedance lying on the locus of constant gap would output the same gap reading. No end user interaction is necessary in this method.

In one form, and referring to FIGS. 18 and 19, the material insensitive method of the digital proximity system 10 includes the steps of: determining a plurality of normalized impedance curves as delineated supra for different materials and preferably storing the curves in a database of the memory means; defining a series of locus lines on the impedance curves that represent the same gap for the different materials; measuring an impedance of the probe located proximate a target material to be monitored, normalizing the measured probe impedance and comparing the normalized probe impedance with the series of locus (the arcuate lines) stored in the database for determining a gap locus that corresponds to the normalized impedance value of the probe wherein the corresponding gap locus reveals a gap value substantially correct for any target material being monitored thereby providing a material insensitive digital proximity system 10.

In another form, the material insensitive method of the digital proximity system 10 includes the steps of: determining a plurality of normalized impedance curves as delineated supra for different materials and defining a series of locus lines on the impedance curves that represent the same gap for the different materials; storing an equation(s) or numerical methods which approximate the arcuate locus lines in the memory means; measuring an impedance of the probe located proximate a target material to be monitored, normalizing the measured probe impedance and using the equations(s) or numerical methods for determining a gap locus that corresponds to the normalized impedance value of the probe wherein the corresponding gap locus reveals a gap value substantially correct for any target material being monitored thereby providing a material insensitive digital proximity system 10.

Note that the material insensitive method described hereinabove can be followed when employing a probe/extension cable combination in place of the probe only.

Specifically, The step of measuring the impedance of the probe located proximate a target in the two former material insensitive methods can further include measuring the impedance of the probe and an extension cable wherein all the subsequent steps are carried out using this measured combination of impedance in place of just the probe impedance and all the previous steps are carried out using a probe/extension cable combination.

In yet another form, and the material insensitive method of the digital proximity system 10 can include the step of mathematically estimating the sensing element or coil impedance of the probe by removing any contribution of impedance from the integral probe cable and the extension cable (if employed). Any contribution of impedance from the integral probe cable and the extension cable (if employed) can be determined from the open/short/load calibration method delineated above.

Figure 20:
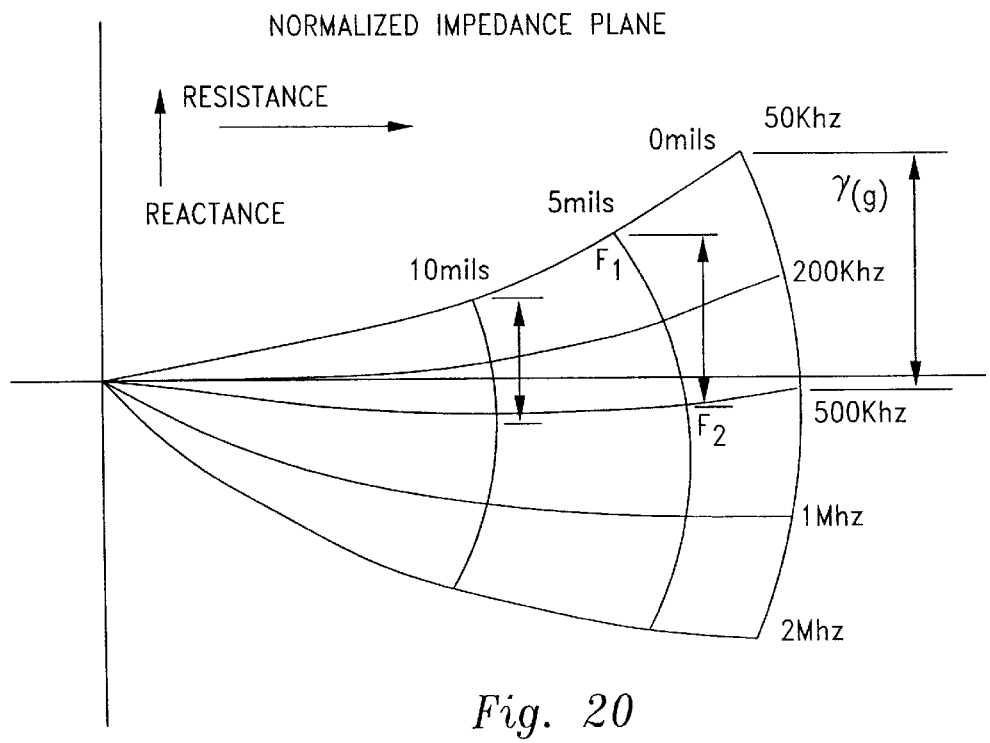
FIG. 20 is a graph showing a normalized impedance plane of resistance and reactance for diagrammatically defining nomenclature of an inductive ratio method according to the instant invention.
Figure 21:
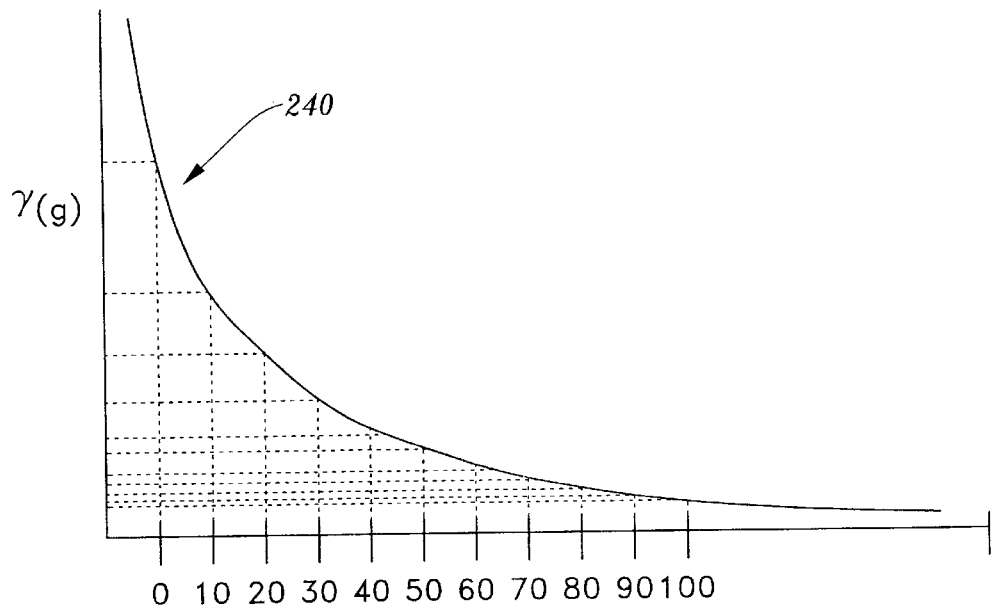
FIG. 21 is a graph showing an inductive ratio as a function of gap for defining nomenclature of the inductive ratio method according to the instant invention.
Figure 22:
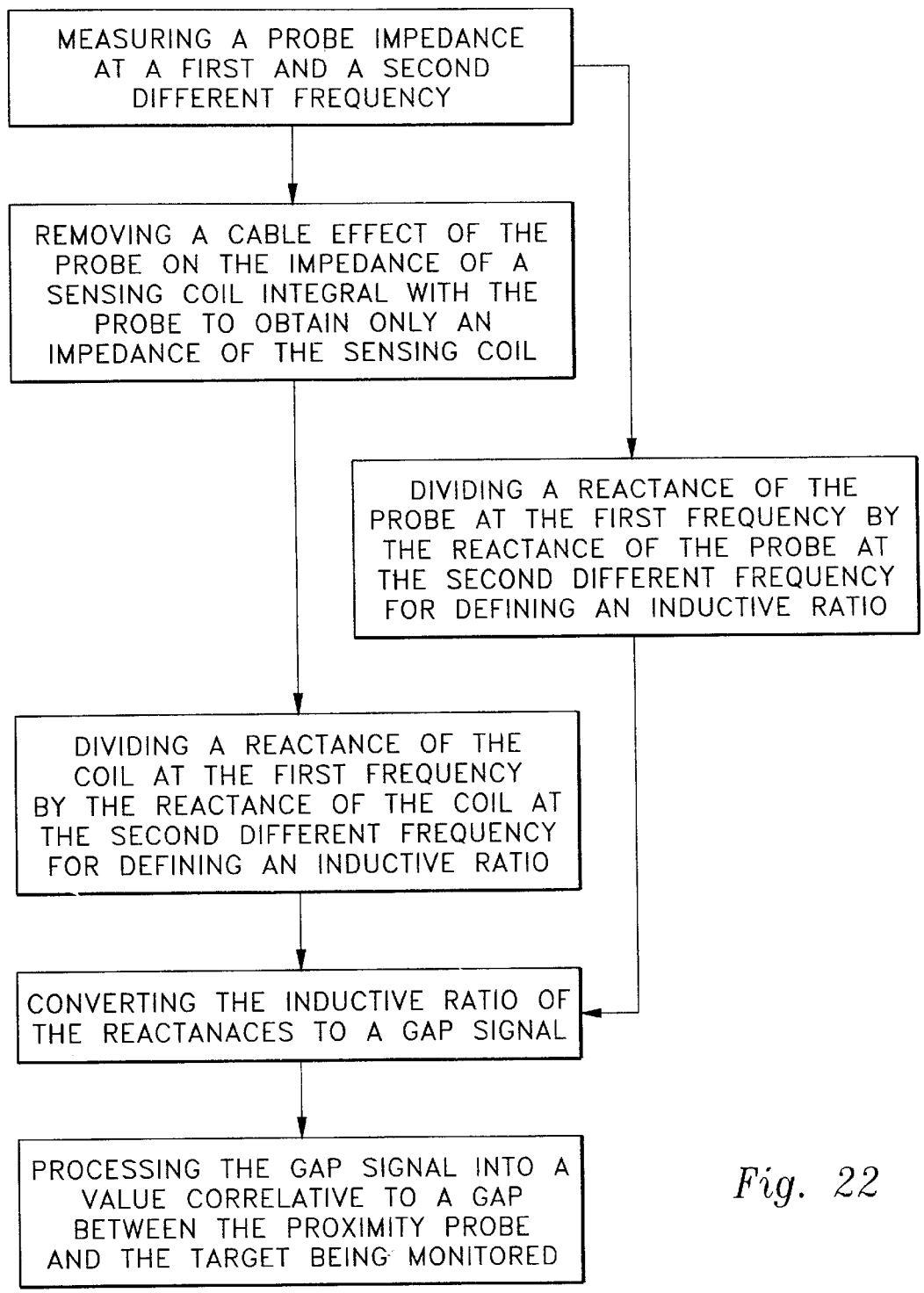
FIG. 22 is a flow chart of an inductive ratio method according to the instant invention.

Referring to FIGS. 20 through 22, the unique inductive ratio method of the instant invention allows a normalized impedance curve to be determined for a specific target without knowing the far gap impedance of the probe coil and thus, without removing the probe from a machine being monitored.

As delineated supra, the far gap impedance is needed to actually determine the normalized impedance of the probe and to develop the normalized impedance curve for a specific target which in turn can be used to determine the gap between the probe and the target being monitored. There is a normalized impedance value for each target at each frequency and gap.

Experiments have shown that normalized impedance diagrams generated from different probes in the same series of transducers have very little variation. This is because the normalizing process used to generate the diagrams removes the variations caused by differences in resistance and inductance between the different coils. All that remains is the probe geometry and the target material. Coil geometry is very consistent in regards to how the target interacts with the coil. In fact, water in a coil will cause very little error in the normalized impedance diagram until the probe gets so wet it's almost shorted out.

Unfortunately, one can not use this technique directly to measure probe gap because it depends on knowing the far gap impedance of the probe coil, which can not be determined without removing the coil from a machine being monitored by the probe. Accordingly, there is a need for a method and apparatus which solves these problems.

Referring to FIGS. 20 through 22, the digital proximity system 10 includes the unique inductive ratio method which is based on the normalized impedance response, but is independent of the unknown variables.

In general, and assuming that the probe is mounted in a machine at an unknown gap, an initial step of the inductive ratio method is to measure the impedance of the probe at two different frequencies $f_1$ and $f_2$ (please see FIG. 20). Thus, the impedance at $f_1$ is X1=(R1+jwL1) and the impedance at $f_2$ is X2=(R2+jwL2). Next, the instant invention assumes that the far gap impedance at f1 is r1+jwl1 and the far gap impedance at f2 is r2+jwl2. Then, the normalized impedance is calculated as follows:

| For X1: R1n = (R1−r1)/w1l1 | w1L1n = w1L1/w1l1 |
|---|---|
| For X2: R2n = (R2−r2)/w2l2 | w2L2n = w2L2/w2l2 |

As noted above the resistance is unreliable and therefore, the focus will be on the reactance measurement. In addition, it was noted supra that the far gap is unknown and as a result, w1L1n and w2L2n can not be calculated because l1 and l2, inductances at far gap, are unknown.

However, applicant has discovered that a function can be defined to remove the unknown variables. Specifically, applicant has discovered that if a function is defined to equal a normalized reactance at $f_1$ divided by a normalized reactance at $f_2$ the unknowns can be made to disappear. This function can be defined as, for example, an inductive ratio function γ. Therefore γ=(w1L1n/w2L2n) and from the equations for X1 and X2 hereinabove we have the following:

$$(w1L1n/w2L2n)=(w1L1/w1l1)/(w2L2/w2l2) \text{ and thus,}$$

$$(w1L1n/w2L2n)=(w1L1/w2L2)*(w2/w1)*(l2/l1),$$

wherein the first term on the right side of the equation can be measured by the system 10 or an impedance meter; the second term is the known frequencies and the third term is the inductances at far gap which changes very little over frequency and therefore can be approximated as equaling one.

This function corresponds to using the change in inductance between two frequencies at one gap to determine the actual gap. A curve 240 of the function γ versus gap can be precomputed and the value determined in the measurement above can be used to estimate the gap of the probe in question. Graphically, this is shown in FIG. 21 wherein γ which is depicted as γ(g) is plotted versus gap. In other words, the gap is equal to the measured reactance at f1 divided by measured reactance at f2 times the frequency at f2 divided by the frequency at f1. Therefore, the instant invention provides a method (generally depicted in FIG. 22) that defines a function of gap that is primarily a function of probe geometry without it's actual inductance or resistance being a major factor.

Moreover, the inductive ratio method can further include the step of mathematically removing the effect of the integral cable of the probe on the impedance of the sensing coil, mathematically removing the effect of the extension cable on the impedance of the probe, or mathematically removing the effect of both the integral cable of the probe and the extension cable on the impedance of the sensing coil using the cable calibration methods described hereinabove.

For example, the inductive ratio method can further include the step of mathematically removing the effect of both the integral cable of the probe and the extension cable on the impedance of the sensing coil (using the cable calibration methods described hereinabove) to obtain only the impedance of the coil after initially measuring the impedance of the probe at two different frequencies $f_1$ and $f_2$. As a result, the impedance at $f_1$ defined as $X1=(R1+jwL1)$ and the impedance at $f_2$ defined as $X2=(R2+jwL2)$ hereinabove can also be used to define the impedances of only the sensing coil at two different frequencies. Thus, the method defined supra can be identically carried out with the addition of this cable compensation step.

Specifically, the inductive ratio method can include the following steps. First, measuring the uncompensated impedance of the probe and extension cable (if employed) at two different frequencies $f_1$ and $f_2$. Second, determining compensation factors from open/short/load calibration tables. Since this method can be generally done at fixed frequencies, the compensation factors may be pre-computed. Third, compensating the measured impedances using the coefficients determined from the open/short/Load method. Fourth, mathematically removing the cable effect(s) on measured impedance so that only the sensing coil impedance remains. Note that in a system that is trimmed for this method, the cables will be physically trimmed so that they match as closely as possible the cable compensation values programmed into the system 10. Fifth, computing the function γ, which is the reactance of the coil at one frequency divided by the reactance of the same coil at a different frequency. Sixth, determining gap from the value γ, and seventh, iteratively repeating the previous six steps.

The advantage of the inductive ratio method according to the instant invention is that many of the variables that affect the impedance measurement are eliminated using this method. Some of the variables eliminated are: the probe resistance, the probe inductance, the value of the known resistance in the detector, the voltage magnitude and phase driven into the known resistor and the reference driving the analog to digital converters.

As noted, this method determines gap in a way that is very insensitive to the series resistance of the coil. This is important because most probe system failures cause a change in series resistance, but not in coil inductance. Errors like: loose connectors, temperature variations, and most significantly water in the probe all cause a change in resistance, but little or no change in reactance. The only single ended error sources left are the probe geometry and the reference driving the digital to analog output.

Additionally, this method can be used as a way of detecting the gap of probe that is installed in the machine, detecting the gap of a probe that may be contaminated with water thereby precluding the resistive term of impedance from being used and/or detecting the gap of a probe wherein a far gap impedance can not be estimated to normalize the measured impedance of the probe. Furthermore, this method can be used to provide redundant measurements of gap in the digital proximity system 10 thereby providing a cross check of actual system performance.

In operation, and referring to the drawings, the proximity probe 12 is typically coupled proximate a target to be monitored, for example, a rotating shaft of a machine or an outer race of a rolling element bearing for monitoring the gap therebetween. Therefore, the probe is strategically coupled to the machine for sensing raw dynamic data that is correlative to the spacing between the probe and the target of the machine being monitored to obtain a signature of the status of the machine.

The dynamic voltages $V_1$ and $V_2$ are continuously converted into periods or cycles of digital samples. The periods or cycles of digital samples are subsequently convolved into corresponding periods or cycles of complex voltage numbers $V_{1C}$ and $V_{2C}$ which are used to determine dynamic impedance values of the probe 12. The dynamic impedance values are typically correlated to gap values correlative to the displacement motion and position of the conductive target material being monitored relative to the probe. The impedance or gap values may be outputted to an analog output via a digital to analog converter 142. The analog output may be in the form of alarms, circuit breakers, etc. These devices are set to trip when the analog output is outside a user set nominal operating range.

The impedance or gap values may be outputted to a host computer 146 and/or to a processor 160 for further processing for the use of monitoring rotating or reciprocating machinery. In one form, and referring to FIGS. 1 and 3, the digital proximity system 10 includes a communications link 144, for example, a serial communications channel or interface which is operatively coupled to the digital signal processor means 110 for outputting signals to the host computer 146 and thus, to an end user. The serial communications channel 144 allows the digital samples or the convolved signals to be outputted from the digital signal processor means 110 to the remote computer 120 without sending the full dynamic information of the original signals $V_1$ and $V_2$ thereby providing an important advantage of reducing the bandwidth of the communication signals. Additionally or alternatively, the impedance or gap values may be outputted to the processor 160 where the values may be continuously accumulated, processed and/or stored and, at any time, can be transmitted to the host computer 146 for further processing and/or output to an end user for the use of monitoring rotating or reciprocating machinery.

Furthermore, the digital signal processor means 110 or the processor 160 may perform signal reduction on the digitized impedance or gap values and then output that information to the remote computer 120 via the serial communications link 118 and/or directly to the digital to analog converter 116. For example, the digital signal processor means 110 or the processor 150 may perform signal reduction in the from of peak to peak amplitude detection, DC gap detection, nX amplitude and phase detection and/or spectral content detection.

Moreover, memory means 120 can include an EEPROM tied to the DSP such that when the DSP first powers up it loads operating information and parameters stored in EEPROM into its internal memory 112. The EEPROM can be replaced with a dual port RAM (DPRAM) and as far as the DSP is concerned it looks like an EEPROM. In one form, the processor means 160 is coupled to the DPRAM and in turn, DPRAM is coupled to the DSP. Thus, when the DSP is held in recess the processor means 160 can load programming and data into the DPRAM and once the DSP is released the DSP pulls everything out from the DPRAM and into internal memory 112.

The system 10 provides timely, meaningful and actionable information to end users. The behind the scenes activities that the system 10 may perform to verify its own condition and validate its data is a process which is not one task or idea, but a process by which the system 10 self-validates. The system 10 enables some level of additional self-checking over existing systems. It is these aspects of the aforementioned process, which are as follows:

1. The system 10 can self identify target materials (or designed to work with all metals) thereby resulting in a system 10 which be cannot mis-calibrated when put into operation.

2. Multiple signal processing algorithms may be run at the same time on the system 10. This allows cross-checking the different methods described above to verify proper system operation with the same eddy current probe. As an example, the inductive ratio method can be used to help tell if a probe is wet while it is still in the machine.

3. The system 10 input bandwidth is sufficiently high to be able to detect intermittent connections on the probe and extension cable. For example, an open or short will cause a sudden change in voltage at the analog to digital converters. This change is faster than a rotor can move to cause a change in analog to digital readings. Thus, by checking the slew rate of the signal we can check to see if it is faster than the rotor can move. If it is to fast, the cause must be an electrical fault like an intermittent connector. If the bandwidth was too slow, we could not differentiate the problems.

4. The memory allows the system 10 to know if it has an intermittent on its input power wiring and the digital communications channel or link allows it to communicate its problems to an asset management software system at the host. As an example, the system 10 know that it reset due to power glitches three times in the last hour and digitally communicates that to an asset management system (Host computer) which could check to see if the power had actually been turned off. If not, there is trouble with the wiring.

5. The digital communications channel and the memory associated with the DSP and/or the CPU allows the system to generate it's own maintenance requests.

6. The memory associated with the DSP and/or the CPU, and the digital communications channel allows the system to store a complete record of it's own checkout following installation. This allows the system to be able to communicate back up to the management software whether or not it's been subject to a loop check, when that occurred and the results of that test when it was run.

7. The memory associated with the DSP and/or a CPU, and the digital communications channel allows the system to be used with a portable checkout device that includes a bar code reader for recording serial numbers on probes and extension cables. This allows the configuration software to upload which probe is tied to which extension cable from the system 10. Standard labels could also be provided indicating bearing number and X,Y, spare X, spare Y to link these into the system 10. This helps eliminate translation errors caused by having a user write the data down and then keypunching them into the system 10.

8. Including the complete signal chain in the system 10 software (including serial numbers) allows remote access for a product service group to look for configuration errors or trace repairs that may need to be done. It also allows spares to be ordered without having to have someone go and look at the installation.

9. The barcode technology can work the other way when the systems 10 is disconnected and re-assembled. The portable device can request the probe/extension cable serial numbers from the system 10 and then make a tone or a beep representing good or bad as the technician scans barcodes looking for the right one to tie into the system.

10. The system 10 can include a signal processing algorithm that is essentially immune to gap and very sensitive to material condition (sort of an electrical runout measurement system). This can be used to create a waveform representing the material condition of the shaft. This pattern may be compared between X-Y pairs to help verify that the probe orientation and direction of rotation are all configured correctly.

11. The system 10 can stop driving the probe and extension cable, but still measure the voltage developed across it due to ground loops or RFI. This can be done during system assembly as a check.

12. The system 10 can measure the wideband RMS voltage and compare that to the one frequency that the system 10 is measuring at to see if noise is being injected into the signal for some reason. Note, the system 10 may not be getting bad readings because of the narrow bandwidth and the system 10 is still able to detect that the signal noise is there. This can be correlated to the "bump in the night" data that may cause some kind of glitch. This is very similar to a NOT 1X measurement made, however the system can discern exactly how much synchronous signal is being driven through the system so any NOT 1X will be due to harmonic distortion (which should not change unless a hardware problem occurs) and outside noise. If necessary, one could compute spectra of the signal and separate out harmonic distortion (an internal hardware problem) with internally or externally generated noise. It's also possible to compute the spectra using different sampling frequencies and figure out the exact frequency that's causing trouble (assuming it's not wideband noise). This is because one will be able to identify where the foldover frequencies occur and can identify the aliased frequencies.

13. The 1X signal may also be used to help verify probe orientation and direction of rotation.

14. An internal timestamped event list may be maintained in the system to document when changes were made to it's configuration. This can be used to help verify that there were no NOT OK times from the time of some recent event back to its last verification cycle.

Furthermore, the system 10 also provides a solution to a need for more systems to be used as references (working standards) during manufacturing process of analog systems. The stability of the system 10 increases at a result of at least the following three reasons: One, the system 10 design is inherently more stable because it depends on the ratiometric measurements used in the Analog to Digital (A-D) converters, rather than on the bias through a PN junction operating on, for example, a 1 MHz signal. Two, the tank inductor in the analog system has been eliminated and replaced with a mathematical equation. The tank inductor is the most sensitive component and has a tendency to "walk" over time. "Walk" refers to a ferrite core inductor's tendency to experience short and long term drift in its impedance value. It is not known what causes it, but it is known that it's there. Three, it is possible to perform open/short/load calibration on every working standard system 10 at the beginning of the day or work order to re-zero it's response.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A device for digitally measuring electrical impedance, comprising in combination:

a network including a first electrical component and a second electrical component serially connected;

a signal generating means operatively coupled to said network for driving a current through said serially connected components;

means for sampling a first voltage impressed across said network and a second voltage impressed across said second component into digitized voltages;

means for convolving each said digitized voltage with a digital waveform for forming a first complex number and a second complex number correlative to said first voltage impressed across said network and said second voltage impressed across said second component respectively;

means for determining a ratio of said second complex number to a difference between said first and said second complex number, and means for calculating an electrical impedance of said second component by multiplying said ratio by a value of said first component wherein said electrical impedance of said second component is digitally measured.

2. The device of claim 1 wherein said convolving means includes means, operatively coupled to said sampling means, for digitally multiplying each of said digitized voltages with a digitized sine wave and a digitized cosine wave.

3. The device of claim 2 wherein said digitized sine wave and said digitized cosine wave are pulled from a memory means operatively coupled to said convolving means.

4. The device of claim 3 wherein said convolving means further includes means for transforming the results of multiplying each of said digitized voltages with said digitized sine wave and said digitized cosine wave into orthogonal DC components which define a real component magnitude and an imaginary component magnitude for each of said first complex number and said second complex number correlative to said first voltage impressed across said network and said second voltage impressed across said second component.

5. The device of claim 4 wherein said determining means includes a digital signal processor operatively coupled to said convolving means for determining said ratio of said second complex number to said difference between said first and said second complex number, and wherein said calculating means includes said processor for calculating said unknown electrical impedance of said second component by multiplying said ratio by said known value of said first component.

6. The device of claim 5 wherein said signal generating means includes at least one frequency/phase programmable signal generator operatively coupled to said digital signal processor and said network for receiving digital commands from said digital signal processor for generating a frequency/phase programmable signal for driving said current through said serially connected components at a digitally programmed frequency/phase defined by said digital signal processor.

7. The device of claim 6 further including a timing control means for triggering said sampling means to sample said first voltage and said second voltage at a rate which maintains a substantially constant phase relationship between said programmable signal and the sampled voltages.

8. The device of claim 1 wherein said first electrical component includes a resistance means having a known resistance value.

9. The device of claim 8 wherein said second electrical component includes a proximity probe comprising a sensing coil and a probe cable operatively coupled to said sensing coil, said proximity probe having an unknown impedance value and located proximate a conductive target material to be monitored for position.

10. The device of claim 9 wherein said means for calculating said electrical impedance of said second component by multiplying said ratio by said value of said first component includes calculating the electrical impedance of the proximity probe by multiplying said ratio by said know resistance value wherein said unknown electrical impedance of said proximity probe is digitally measured.

11. A device of claim 10 further including means for correlating the digitally measured impedance value of the proximity probe to a value defining a gap between said proximity probe and said metallic target being monitored.

\* \* \* \* \*